United States Patent
Mannino et al.

(10) Patent No.: US 11,123,295 B2
(45) Date of Patent: Sep. 21, 2021

(54) **ENCHOLEATED ANTIFUNGAL COMPOUNDS FOR CENTRAL NERVOUS SYSTEM DELIVERY AND TREATMENT OF *CRYPTOCOCCUS* INFECTIONS**

(71) Applicant: MATINAS BIOPHARMA NANOTECHNOLOGIES, INC., Bedminster, NJ (US)

(72) Inventors: Raphael J. Mannino, Glen Gardner, NJ (US); Ruying Lu, New Providence, NJ (US); Doug F. Kling, Lebanon, NJ (US)

(73) Assignee: MATINAS BIOPHARMA NANOTECHNOLOGIES, INC., Bedminster, NJ (US)

( * ) Notice: Subject to any disclaimer, the term of this patent is extended or adjusted under 35 U.S.C. 154(b) by 0 days.

(21) Appl. No.: 16/312,047

(22) PCT Filed: Jul. 12, 2017

(86) PCT No.: PCT/US2017/041750
§ 371 (c)(1),
(2) Date: Dec. 20, 2018

(87) PCT Pub. No.: WO2018/013711
PCT Pub. Date: Jan. 18, 2018

(65) Prior Publication Data
US 2020/0121601 A1    Apr. 23, 2020

Related U.S. Application Data

(60) Provisional application No. 62/361,351, filed on Jul. 12, 2016, provisional application No. 62/513,800, filed on Jun. 1, 2017.

(51) Int. Cl.
*A61K 9/127*    (2006.01)
*A61P 31/10*    (2006.01)
(Continued)

(52) U.S. Cl.
CPC .......... *A61K 9/1274* (2013.01); *A61K 9/0053* (2013.01); *A61K 9/0085* (2013.01);
(Continued)

(58) Field of Classification Search
CPC ................ A61K 9/1274; A61K 9/0053; A61K 9/0085; A61K 47/24; A61K 31/7048;
(Continued)

(56) References Cited

U.S. PATENT DOCUMENTS 5,837,254 A    11/1998    Chen
5,925,616 A    7/1999    Whittemore
(Continued)

FOREIGN PATENT DOCUMENTS

CA    2480265 A1    10/2003
CA    2504329 A1    5/2004
(Continued)

OTHER PUBLICATIONS

International Search Report and Written Opinion dated Sep. 28, 2017 from International Application No. PCT/US2017/041750 (Authorized Officer, Lee W. Young), 11 pages.
(Continued)

*Primary Examiner* — Gollamudi S Kishore
(74) *Attorney, Agent, or Firm* — MH2 Technology Law Group, LLP

(57) ABSTRACT

The present application is directed to a cochleate composition including one or more cochleates and at least two antifungal compounds selected from amphotericin B, 5-flucytosine, fluconazole, ketoconazole, ravuconazole, albaconazole, itraconazole, posaconazole, isavuconazole and/or voriconazole. Methods of using the antifungal cochleate formulations are also disclosed.

17 Claims, 8 Drawing Sheets

(51) Int. Cl.
    *A61K 9/00*              (2006.01)
    *A61K 31/7048*       (2006.01)
    *A61K 47/24*           (2006.01)
    *A61K 31/513*        (2006.01)

(52) U.S. Cl.
    CPC .......... *A61K 31/7048* (2013.01); *A61K 47/24* (2013.01); *A61P 31/10* (2018.01); *A61K 31/513* (2013.01)

(58) Field of Classification Search
    CPC ................ A61K 31/513; A61K 9/0019; A61K 9/0043; A61K 31/4196; A61K 31/496; A61K 31/506; A61K 9/127; A61K 2300/00; A61P 31/10
    See application file for complete search history.

(56) References Cited

U.S. PATENT DOCUMENTS

| | | |
|---|---|---|
| 2005/0013854 A1 | 1/2005 | Mannino et al. |
| 2005/0124536 A1 | 6/2005 | Ikeda et al. |
| 2007/0141135 A1* | 6/2007 | Balu-lyer ................. B82Y 5/00 424/450 |
| 2009/0087480 A1* | 4/2009 | Nomura ............... A61K 31/445 424/450 |
| 2010/0210575 A1* | 8/2010 | Kwon ..................... A61P 31/00 514/31 |
| 2012/0037154 A1* | 2/2012 | Gallem ............. A61M 15/0015 128/200.16 |
| 2013/0089527 A1* | 4/2013 | Fong ........................ A61K 9/10 424/93.7 |
| 2014/0220108 A1 | 8/2014 | Lu et al. |
| 2015/0140074 A1 | 5/2015 | Mannino et al. |

FOREIGN PATENT DOCUMENTS

| | | |
|---|---|---|
| JP | 2003529557 A | 10/2003 |
| JP | 2015528021 A | 9/2015 |
| WO | 01/52817 A2 | 7/2001 |
| WO | 2004/092123 A2 | 10/2004 |
| WO | 2010/091090    * | 8/2010 |

OTHER PUBLICATIONS

Partial Supplementary European Search Report dated Feb. 4, 2020 from European Patent Application No. 17828400.6, 15 pages.
David S. Perlin, "Amphotericin B cochleates: A vehicle for oral delivery", Current Opinion in Investigational Drugs, Feb. 2004, vol. 4, No. 2, pp. 198-201.
Leila Zarif, "Elongated supramolecular assemblies in drug delivery", Journal of Controlled Release, May 17, 2002, vol. 81, No. 1-2, pp. 7-23.
Boulware et al., "Prognosis and management of cryptococcal meningitis in patients with human immunodeficiency virus infection", Neurobehavioral HIV Medicine, Jun. 1, 2012, , vol. 4, p. 45-61.
Brizendine et al., "Cryptococcal Meningitis: Current Approaches to Management in Patients With and Without AIDS", Current Infectious Disease Reports, May 15, 2010, vol. 12, No. 4, pp. 299-305.
Srichatrapimuk et al., "Integrated therapy for HIV and cryptococcosis", AIDS Research and Therapy, Nov. 29, 2016, vol. 13, No. 42, 15 pages.
Office Action dated Mar. 2, 2021 for corresponding Japanese Patent Application No. 2019-500624, 8 pages with English translation.
Perfect et al., "Clinical Practice Guidelines for the Management of Cryptococcal Disease: 2010 Update by the Infectious Diseases Society of America", Clinical Infectious Diseases, 2010, vol. 50, No. 3, pp. 291-322.
Office Action dated Dec. 15, 2020 from corresponding Chinese Patent Application No. 201780056037.8, 18 pages with English translation.

* cited by examiner

ENCHOLEATED ANTIFUNGAL COMPOUNDS FOR CENTRAL NERVOUS SYSTEM DELIVERY AND TREATMENT OF *CRYPTOCOCCUS* INFECTIONS

CROSS REFERENCE TO RELATED APPLICATIONS

This application is a U.S. National Stage application of PCT/US2017/041750 filed 12 Jul. 2017, which claims the benefit of and relies on the filing date of U.S. Provisional Application No. 62/361,351, filed 12 Jul. 2016 and U.S. Provisional Application No. 62/513,800, filed on 1 Jun. 2017; the entire disclosure of each application is incorporated herein by reference.

FIELD

This application relates generally to cochleate compositions comprising antifungal agents and methods of administering the same to treat fungal infections, in particular, fungal infections caused by *Cryptococcus* spp.

BACKGROUND

Cryptococcosis is an opportunistic fungal infection causing an estimated 1 million cases and 625,000 deaths per year due to central nervous system (CNS) disease among patients with human immunodeficiency virus worldwide. The vast majority of cases globally were caused by *Cryptococcus neoformans*, compared to the more geographically restricted *Cryptococcus gattii*. Although cryptococcosis is most often associated with HIV infection, in many centers, especially in more developed countries, the majority of cases occur among non-HIV-infected individuals including transplant recipients; patients who are receiving immunosuppressive agents such as glucocorticosteroids, cytotoxic chemotherapy, TNF-α inhibitors, and other disease modifying agents; and a heterogeneous group of patients with underlying disorders such as organ failure syndromes, innate immunologic problems, common variable immunodeficiency, and hematologic disorders. Moreover, in many centers, up to 20% of cases of cryptococcosis occur in phenotypically "normal" or otherwise clinically non-immunocompromised patients.

Cases of cryptococcosis are thought to start with inhalation of fungal cells from the environment. Within the lung, *Cryptococcus* spp. can cause pneumonia in immunosuppressed patients, but in immunocompetent hosts, the fungal cells are typically either cleared by the immune system or establish an asymptomatic latent infection. On subsequent immunosuppression, this latent infection can then disseminate to other tissues, most notably the central nervous system (CNS). Once established in the CNS, cryptococcosis causes an overwhelming infection of the meninges and brain tissue that is frequently accompanied by raised intracranial pressure. Without rapid and effective treatment, CNS infection is invariably fatal.

The cornerstone of treatment of cryptococcal meningoencephalitis is amphotericin B deoxycholate (AmBd), developed in the 1950s, which exerts its fungicidal effect both by generating pores in the cell membrane and by inducing cell death via oxidative damage. AmBd is sometimes combined with 5-Flucytosine (5-FC) to provide a combination therapy that can improve the 10-week survival of patients compared with treatment using AmBd alone. This combination remains the recommended 'gold standard' induction treatment, but presents substantial challenges as AmBd has notable toxicities and its IV formulations require sophisticated electrolyte monitoring, and intravenous catheters that have precluded the use of this medication in resource poor settings.

To circumvent the problems associated with AmBd and 5-FC combination therapies, the combination of fluconazole with 5-FC has been considered. Fluconazole has good oral bioavailability and can penetrate the cerebrospinal fluid, which also makes it a good candidate for maintenance therapy after initial treatment. However, fluconazole is a fungistatic compound (rather than a fungicidal compound) and so it is less effective at pathogen clearance and, thus, is not recommended for initial therapy. Consequently, there remains a clear and continued need to provide Cryptococcosis treatments that are orally available, effective, and which may be provided at reduced cost.

SUMMARY

The present inventors have surprisingly discovered that encochleated amphotericin B (also referred to herein as AmB), which is orally available and has low toxicity, in combination with orally administered 5-Flucytosine is as effective at clearing *Cryptococcus* spp. in mouse as is systemically administered amphotericin B deoxycholate and orally administered 5-Flucytosine.

Moreover, the present inventors have shown that encochleated amphotericin B is delivered to the brain where the most severe *Cryptococcus* spp. infections occur. Thus, the present compositions, which may be conveniently orally administered, have the potential to open up vast areas of the developing world to the potent fungicidal activity of amphotericin-based therapeutics for the treatment of Cryptococcosis. These and other benefits of the instant antifungal cochleates are further described herein.

The present disclosure is directed to a cochleate composition including: one or more cochleates and a therapeutically effective amount of at least two antifungal compounds selected from, for example, amphotericin B, 5-Flucytosine (also referred to herein as 5-FC and flucytosine), fluconazole, ketoconazole, ravuconazole, albaconazole, itraconazole, posaconazole, isavuconazole and/or voriconazole. In some embodiments, the at least two antifungal compounds are amphotericin B and 5-Flucytosine. Additional antifungal compounds are described herein.

In some embodiments, the cochleates are formulated for mucosal administration, such as oral administration or intranasal administration. In other implementations, the cochleates are formulated for intravenous administration. In some implementations, the cochleates are formulated for intrathecal administration.

In some embodiments, only one of the at least two antifungal compounds are formulated as a cochleate. In other implementations, at least two antifungal compounds are formulated as a cochleate. In some implementations, the at least two antifungal compounds are formulated within the same cochleate. In other implementations, the at least two antifungal compounds are each formulated in a different cochleate.

In some embodiments, one or more of the cochleates described herein is a geodate cochleate as also described herein.

In some embodiments, one or more of the cochleates described herein includes a lipid component, the lipid component including soy phosphotidylserine in an amount ranging from about 30%-70% by weight, more typically 40%-

70% by weight, more typically 40%-60% by weight, more typically 45%-55% by weight, more typically 45%-60% by weight and most typically 45% to about 55% by weight.

The present disclosure is also directed to a method of treating or preventing an infection due to a *Cryptococcus* spp., which method includes: orally administering to a subject in need thereof a formulation including a cochleate, wherein the cochleate includes amphotericin B. In some embodiments, the formulation is administered daily for at least 7 days, at least 14 days, at least 21 days, or at least 28 days. In some embodiments, the method further includes administering 5-Flucytosine to the subject. In some embodiments, the 5-Flucytosine is administered orally. In some embodiments, the 5-Flucytosine is administered daily for at least 7 days, at least 14 days, at least 21 days, or at least 28 days.

The present disclosure is also directed to a method of treating or preventing an infection due to a *Cryptococcus* spp., which method includes: administering to a subject in need thereof a formulation including a cochleate composition, wherein the cochleate composition includes at least two antifungal compounds, wherein the at least two antifungal compounds are selected from amphotericin B, 5-Flucytosine, fluconazole, ketoconazole, ravuconazole, albaconazole, itraconazole, posaconazole, isavuconazole and/or voriconazole, wherein at least one of the at least two antifungal compounds is formulated as a cochleate. In some embodiments, the at least two antifungal compounds are amphotericin B and 5-Flucytosine. Additional antifungal compounds are described herein. In some embodiments, the antifungal compounds are delivered to the brain.

In some embodiments, the infection involves skin, lung, prostate and/or central nervous system. In some embodiments, the infection is cryptococcal meningeoencephalitis. In some embodiments, the infection is cryptococcal meningitis.

In some embodiments, the *Cryptococcus* spp. is *Cryptococcus neoformans*. In some embodiments, the *Cryptococcus* spp. is *Cryptococcus gattii*.

In some embodiments, the administration is oral, intranasal, intrathecal or intravenous. In some embodiments, the cochleate formulation is orally administered and the antifungal compounds are delivered to the brain.

In some embodiments, the subject is a human. In some embodiments, the subject has HIV/AIDS, lymphoma, cirrhosis of the liver or has received an organ transplant.

Also provided herein is a method of treating or preventing an infection due to a *Cryptococcus* spp., which method includes: administering to a subject in need thereof a formulation including a cochleate, wherein the cochleate includes an antifungal compound, wherein the antifungal compound is selected from at least one of 5-Flucytosine, fluconazole, ketoconazole, ravuconazole, albaconazole, itraconazole, posaconazole, isavuconazole and/or voriconazole. Additional antifungal compounds are described herein.

In some embodiments, preventing an infection due to a *Cryptococcus* spp., includes preventing a recurrence of infection. In some embodiments, preventing an infection due to a *Cryptococcus* spp., includes treating a mammal or human, wherein the mammal or human is positive for a cryptococcal species antigen (using, for example, an IMMY Inc. (Norman, Okla.) cryptococcal antigen test).

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

DETAILED DESCRIPTION

Figure 1:
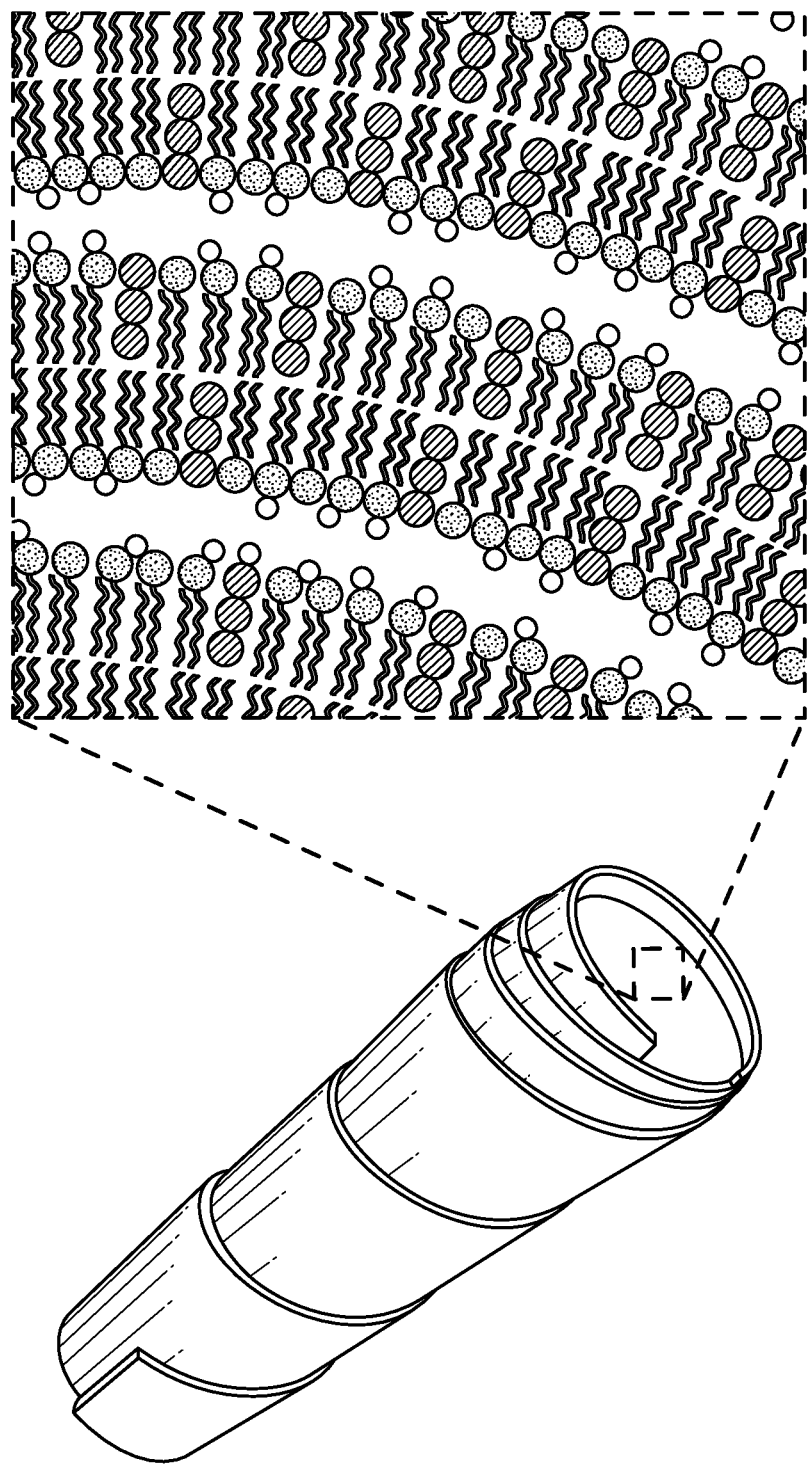
FIG. 1 is a schematic representation of a cochleate. The insert depicts the lipid strata of a cochleate, which contains a phospholipid bilayer (circles and tails), multivalent cation (unshaded circles) and an exemplified cargo moiety (hatched circles) protected within the cochleate.

Reference will now be made in detail to various exemplary embodiments, examples of which are illustrated in the accompanying drawings and discussed in the detailed description that follows. It is to be understood that the following detailed description is provided to give the reader a fuller understanding of certain embodiments, features, and details of aspects of the invention and should not be interpreted as limiting the scope of the invention.

*Cryptococcus* Spp. and Antifungal Compounds

The present disclosure is directed to a cochleate composition comprising: one or more cochleates and at least two antifungal compounds, which are effective against infections caused by *Cryptococcus* spp. As used herein, the term "*Cryptococcus* spp." refers to species of fungi belonging to the genus *Cryptococcus*, which are basidiomycetes encapsulated yeasts. Such infections can be detected, for example, by determining whether or not the subject is positive for a cryptococcal species antigen. Kits for performing such tests are commercially available, e.g., from IMMY Inc. (Norman, Okla.).

Typically, the antifungal cochleates of the instant disclosure are effective against *Cryptococcus neoformans*. *C. neoformans* was originally classified into serotypes A, B, C, D, and AD based on capsular agglutination reactions. More recently, *C. neoformans* has been divided into two varieties: *C. neoformans* var. *grubii* (formerly group A) and *C. neoformans* var. *neoformans* (formerly group D). *C. neoformans* is a ubiquitous pathogen found in most temperate regions of the world, but is commonly found in decaying organic matter and in many soil types, particularly that which has been enriched by animal and bird droppings.

In some embodiments, the antifungal cochleates of the instant disclosure are effective against *Cryptococcus gattii* (formerly groups B and C). *C. gattii* can be divided into four molecular types including VGI, VGII, VGIII, and VGIV. Types VGII can be further divided into VGIIa, VGIIb, and VGIIc subtypes. *C. gattii* can be readily differentiated from *C. neoformans* by plating the isolate on canavanine-glycine-bromothymol (CGB) agar. CGB agar turns blue in the presence of this organism. *C. gattii* is traditionally found in tropical and subtropical geographic regions.

In some embodiments, the *Cryptococcus* spp. of the present disclosure, such as *C. gattii* or *C. neoformans*, more typically, *C. gattii*, for example, *C. gattii* of the VGII lineage, such as VGIIa, are capable of infecting an immunocompetent subject. As used herein, an immunocompetent subject is a subject, typically a mammalian subject, such as a human subject, who has the ability to produce a normal immune response following exposure to an antigen. More typically, however, the *Cryptococcus* spp. of the disclosure are capable of infecting an immunocompromised subject. Immunocompromised subjects include subjects, typically mammalian subjects, such as human subjects, having HIV/AIDS, lymphoma, cirrhosis of the liver, or are organ transplant recipients, subjects who are receiving immunosuppressive agents such as glucocorticosteroids, cytotoxic chemotherapy and/or TNF-α inhibitors.

In some embodiments, the *Cryptococcus* spp. may result in cryptococcal pulmonary disease in a subject. Symptoms of cryptococcal pulmonary disease range from asymptomatic airway colonization to acute respiratory distress syndrome. A subject with pulmonary cryptococcosis may present with mild-to-moderate symptoms, including fever, malaise, cough with scant sputum and/or pleuritic pain. In some embodiments, a subject with pulmonary cryptococcosis may present with pneumonia. In some embodiments, pulmonary disease may occur in the absence of extrapulmonary disease.

In some embodiments, the *Cryptococcus* spp. may disseminate from the lungs to infect the skin, prostate, medullary cavity of bones and/or the central nervous system (CNS) of a subject. Typically, *Cryptococcus* spp. infects the CNS. In some embodiments, *Cryptococcus* spp. result in CNS cryptococcosis, such as meningitis and/or meningoencephalitis. These forms of infection are invariably fatal without appropriate therapy; death may occur from 2 weeks to several years after symptom onset. The most common symptoms of cryptococcal meningitis and meningoencephalitis are headache and altered mental status, including personality changes, confusion, lethargy and coma.

The one or more cochleates of the present disclosure are associated with or loaded with one or more antifungal compound(s), such as at least two antifungal compounds, such as at least three antifungal compounds or such as at least four antifungal compounds. In some embodiments, the one or more antifungal compounds are fungicidal compounds, such as amphotericin B or fungistatic compounds, such as fluconazole and/or 5-flucytosine. As used herein, a "fungicidal" compound is an antifungal compound that kills fungi, rather than simply preventing its growth. In contrast, a "fungistatic" compound as used herein, is an antifungal compound that prevents fungal growth, but does not kill the fungus.

Typically, the cochleates of the present disclosure are associated with or loaded with one or more polyenes, an azole and/or a pyrimidine analogue. Typically, the polyene is amphotericin B. In some embodiments, the azole is fluconazole, ketoconazole, ravuconazole, albaconazole, itraconazole, posaconazole, isavuconazole and/or voriconazole. More typically, the azole is fluconazole. Typically, the pyrimidine analogue is 5-flucytosine.

In some embodiments, other anti-fungal compounds are contemplated for formulation into the instant cochleate composition. Such other anti-fungal compounds include those capable of inhibiting the synthesis of a cell wall component, such as glycosylphosphatidylinositol (GPI)-anchored mannoproteins, e.g., E1210, an orally active molecule, which has in vitro activity against *Cryptococcus* spp. In other embodiments, the anti-fungal compound is an ergosterol synthesis inhibitor, such as VT-1129, which is orally available, shows good CNS penetration and is fungicidal in mouse models of *Cryptococcus* spp. infection.

In other embodiments, the anti-fungal compound is an orally available compound, which is known to exhibit an additive or synergistic activity with fluconazole against *Cryptococcus* spp. Such anti-fungal compounds include amiodarone (a cardiac anti-arrhythmic drug) phenothiazine (an antipsychotic) and taxmoxifen (an estrogen antagonist).

In some embodiments, each of the at least two anti-fungal compounds of the present cochleate composition is in a separate cochleate. In other embodiments, each of the at least two anti-fungal compounds is in the same cochleate. More typically, however, only one of the at least two anti-fungal compounds is encochleated. Even more typically, the encochleated anti-fungal compound is a polyene, such as amphotericin B and the second, third or more anti-fungal compound is unencochleated.

In typical embodiments, the instant cochleate composition includes encochleated amphotericin B and an unencochleated azole and/or an unencochleated pyrimidine analogue. Typically, the unencochleated azole is fluconazole and the unencochleated pyrimidine analogue is 5-Fucytosine. Even more typically, the instant cochleate composition includes encochleated amphotericin B and an unencochleated 5-Flucytosine.

In some embodiments, the instant cochleate composition is formulated for mucosal administration, typically oral and/or intranasal administration, more typically oral administration. However, cochleate compositions formulated for intravenous, subcutaneous, intraperitoneal and intrathecal administration are also contemplated.

Cochleates and Methods of Making the Same

Cochleates are anhydrous, stable, multi-layered lipid crystals which spontaneously form upon the interaction of negatively charged lipids, such as phosphatidylserine, and divalent cations, such as, calcium (see, for example, U.S. Pat. Nos. 4,078,052; 5,643,574; 5,840,707; 5,994,318; 6,153,217; 6,592,894, as well as PCT Publ. Nos. WO 2004/091572; WO 2004/091578; WO 2005/110361, WO 2012/151517, and WO2014/022414, U.S. Patent Publication No. 2014/220108 and Patent Publication No. 2010/0178325; each of which is incorporated fully herein by this reference). Typically, these are referred to as crystal cochleates.

Figure 2:
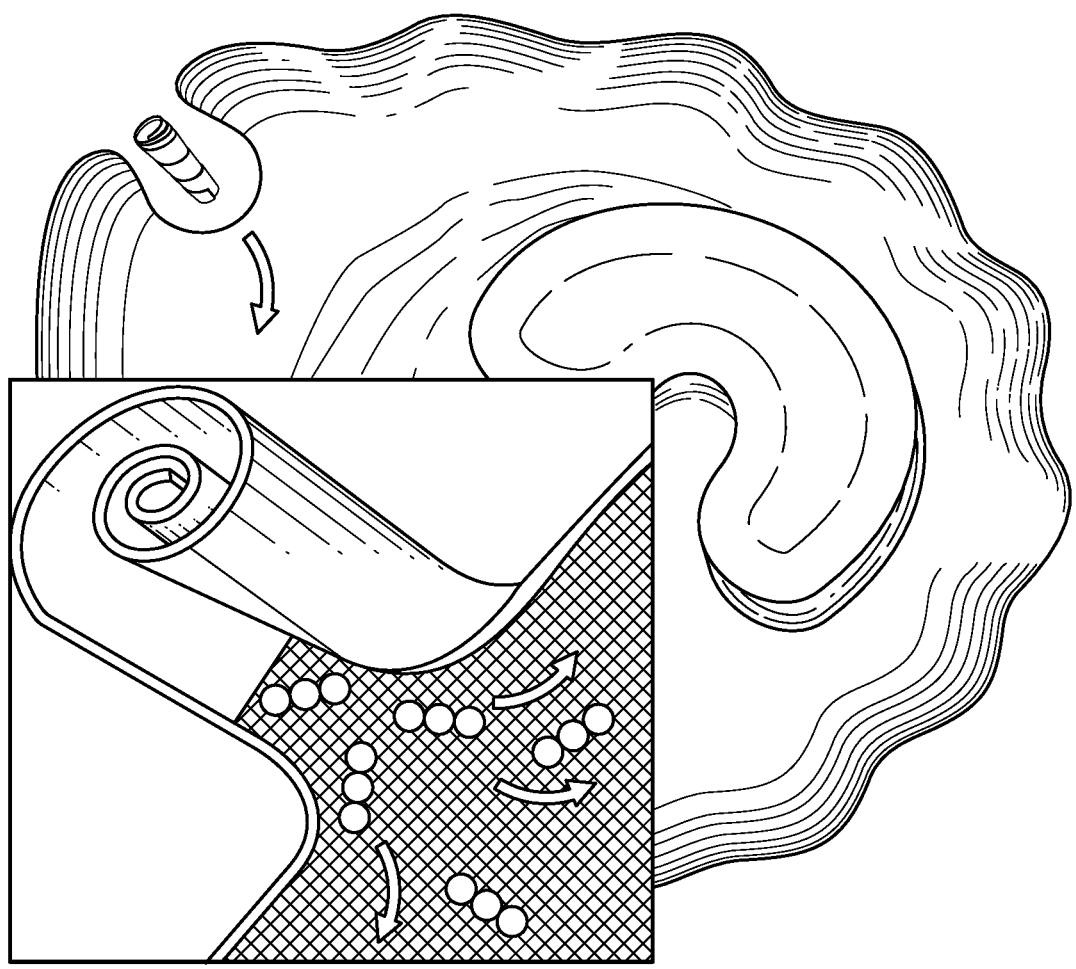
FIG. 2 depicts a schematic of a macrophage engulfing a cochleate and its cargo. The insert depicts the opening of the cochleate and release of the cargo inside the macrophage as described in the detailed description.

Crystal cochleates have a unique multilayered structure consisting of a large, continuous, solid, phospholipid bilayer sheet or strata rolled up in a spiral or as stacked sheets, with no internal aqueous space (FIG. 1). This unique structure provides protection from degradation for associated "encochleated" molecules. Since the entire cochleate structure is a series of solid layers, components within the interior of the cochleate structure remain intact, even though the outer layers of the cochleate may be exposed to harsh environmental conditions or enzymes. Divalent cation concentrations in vivo in serum and mucosal secretions are such that the cochleate structure is maintained. Hence, the majority of cochleate-associated molecules are present in the inner layers of a solid, stable, impermeable structure. Once within the interior of a cell, however, the low calcium concentration results in the opening of the cochleate crystal and release of the molecule that had been formulated into cochleates (FIG. 2). Accordingly, cochleate formulations remain intact in physiological fluids, including mucosal secretions, plasma and gastrointestinal fluid, thereby mediating the delivery of biologically active compounds by many routes of administration, including mucosal, e.g., oral or intransal administration.

Figure 3:
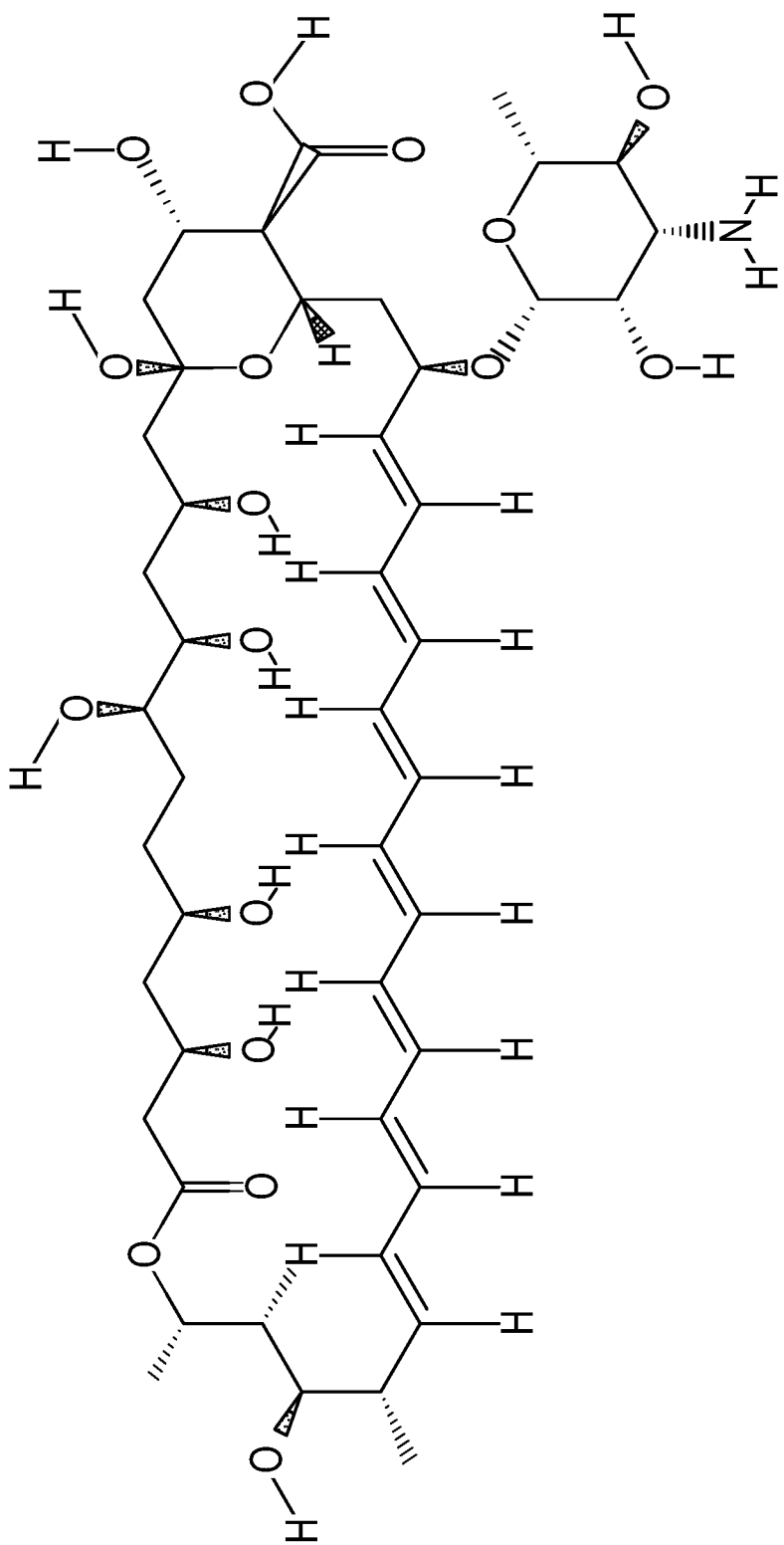
FIG. 3 depicts a structural diagram of amphotericin B.

Typical cochleate structures include a lipid strata comprising alternating divalent cations and phospholipid bilayers that include at least one negatively charged phospholipid. Typically, a cargo moiety, such as an antifungal agent, for example, amphotericin B (FIG. 3) is sequestered within the lipid strata of the cochleate.

Figure 4:
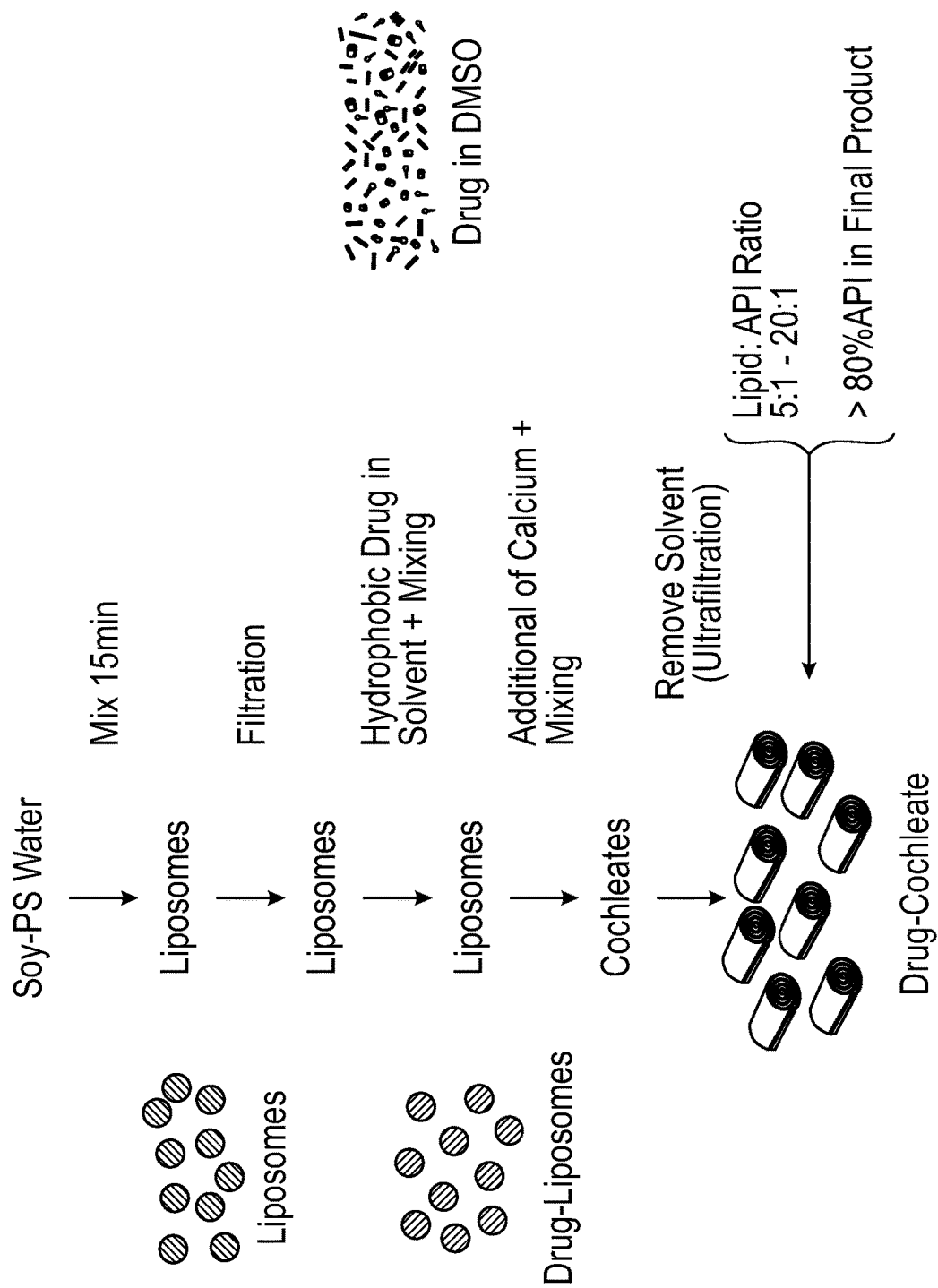
FIG. 4 is a schematic representation of a strategy for making amphotericin B-cochleates (also referred to herein as CAMB).

Cochleates can be made using known methods. In one typical implementation, the method described in U.S. Patent Publication No. 2014/220108 is used to make the cochleates of the present disclosure, which is herein incorporated by reference in its entirety. A summary of this process is shown in FIG. 4. In this method, a hydrophobic antifungal compound, such as amphotericin B, is dissolved in solvent, e.g., dimethylsulfoxide and filtered through e.g., a 0.22 µm filter and combined with e.g., 2000 milligrams 50% soy phosphatidylserine (PS) liposomes in 200 milliliters sterile water (the PS liposomes are first filtered through e.g., 5, 0.8, and 0.45 µm filters) to form liposomes containing the antifungal, such as AmB. To the resultant mixture a cation, such as a multivalent or divalent cation, can be added. The addition of a multivalent or divalent cation results in the collapse of the liposomes, and the formation of the sheets of cation-chelated phospholipid bilayers, which roll up or stack to form cochleates containing antifungal, such as AmB. The antifungal-containing cochleates, such as AmB-containing cochleates, may be dried under lyophilization. Sterile water may be added to the dried powder, anti-fungal cochleates to prepare a suspension. The suspension may be stored at 4° C. in the absence of light.

Other methods for making cochleates containing antifungals include the trapping-high pH method, the trapping-film method and the hydrogel method. In the trapping-high pH method, lipid powder and an antifungal compound, e.g., AmB, are mixed in a lipid/antifungal molar ratio of e.g., 10:1 in an e.g., sterile polypropylene tube. Buffer, e.g., TES [N-Tris(hydroxymethyl)-methyl-2-aminomethane sulfonic acid] (pH 7.4) is added. Multilamellar liposomes are formed after vortexing. The pH is then increased to, e.g., 11.5, by the addition of e.g., 1 N NaOH, to solubilize the antifungal compound, e.g., AmB. The absence of AmB crystals and the presence of liposomes may be monitored by using phase contrast and polarization optical microscopy. Multivalent or divalent cation, such as calcium chloride, is added slowly to the antifungal liposome suspension at a lipid/cation molar ratio of e.g., 2:1, to form the cochleates. The external pH may then be adjusted to pH 7.

In the trapping film method, antifungal compound, e.g., AmB, is dissolved in solvent, e.g., methanol, with brief sonication and the solution is added to lipids in chloroform. The antifungal, e.g., AmB, is readily soluble in the chloroform/methanol mixture. The mixture may then be dried to a film using a rotary evaporator and gently warmed at e.g., 35° C.-40° C., under reduced pressure (1 bar). The dried lipid film may then be hydrated with deionized water and sonicated. The antifungal-liposome size should be around 50 nanometers. To form the cochleates, a multivalent or divalent cation solution, e.g., calcium chloride in solution, is slowly added to the liposome suspension to form the cochleates.

To prepare antifungal cochleates using the hydrogel method, an antifungal compound, such as AmB, is dissolved in methanol and added to lipids in chloroform at, e.g., a 10:1 molar ratio, and the mixture is then dried into a drug-lipid film using a rotary evaporator. The film may then be hydrated with deionized water and the drug-lipid suspension sonicated until small liposomes containing the anti-fungal compounds are obtained. The antifungal-liposome suspension may then be mixed with e.g., 40% w/w dextran-500,000 in a suspension of, e.g., 2/1 v/v dextran/liposome. This mixture is then injected using a syringe into e.g., 15% w/w PEG-8000 under magnetic stirring (800-1000 rpm). An aqueous-aqueous emulsion of antifungal liposomes/dextran droplets dispersed in a PEG continuous phase is obtained. A multivalent or divalent cation solution, e.g., calcium chloride in solution, is then added to the emulsion. Stirring is continued to allow for the slow formation of small-sized antifungal cochleates, which are sequestered in the dextran droplets. The polymer is then washed by the addition of a washing buffer containing e.g., 1 mM $CaCl_2$) and 150 mM NaCl.

As recognized by an ordinary artisan, many parameters, including pH, salt concentration, agitation method and rate, cation type, concentration, and rate of addition, lipid composition, concentration, and ratio of lipid to other material, etc., affect the formulation, and can be varied in order to optimize the encochleation of a particular material.

In some embodiments, a hydrophilic anti-fungal compound, such as 5-FC or an antifungal compound containing a hydrophilic domain, such as fluconazole, may also be formulated into a cochleate. Methods for incorporating such compounds into cochleates are well known in the art and are described, for example, in U.S. Patent Publication No. 2014/220108. Without wishing to be bound to any particular theory, it is believed that hydrophilic molecules or large molecules with hydrophilic domains, such as active pharmaceutical ingredients (APIs) of interest including the anti-fungal compounds of the present disclosure, can be formulated into cochleates in an enhanced manner by associating the API with a lipid domain that acts like a "raft", and which remains intact and imbedded within the cochleate crystal matrix. Such lipids include "neutral lipids" as known in the art and described herein.

In a typical implementation, the multivalent cation described herein, which may be used to collapse the liposomes into cochleates, is a divalent metal cation, such as calcium, zinc, magnesium, and barium. In a more typical implementation, the divalent metal cation is calcium.

In some implementations, the ratio of anti-fungal agent to lipid (wt/wt) ranges from 1:1 to 1:50, or any range in between, such as, 1:2, 1:3, 1:4, 1:6, 1:8, 1:10, 1:12, 1:15, 1:20 and 1:25, typically 1:1 to 1-1:20, such as 1:2.5 to 1:10, typically 1:10.

The liposome used during the formation of the cochleates may be multilamellar (MLV) or unilamellar (ULV), including small unilamellar vesicles (SUV). The concentration of lipid in these liposomal solutions can be from about 0.1 mg/ml to 500 mg/ml. Typically, the concentration of lipid is from about 0.5 mg/ml to about 50 mg/ml, more typically from about 1 mg/ml to about 25 mg/ml.

A size-regulating agent may be introduced during the method of making the cochleate. A size-regulating agent, as used herein, refers to an agent that reduces the particle size of a cochleate. As used herein, the term "particle size" refers to the particle diameter, or in case the particles are not spherical, to the largest extension in one direction of the particle. The particle size of cochleates can be measured using conventional methods, such as a submicron particle size analyzer. In certain embodiments, the size regulating agent is a lipid-anchored polynucleotide, a lipid-anchored sugar (glycolipid), or a lipid-anchored polypeptide. In other embodiments, the size regulating agent is a bile salt, such as oxycholate, cholate, chenodeoxycholate, taurocholate, glycocholate, taurochenodeoxycholate, glycochenodeoxycholate, deoxycholate, or lithocholate. Bile salts are bile acids compounded with a cation, usually sodium. Bile acids are steroid acids found predominantly in the bile of mammals and are commercially available.

In certain embodiments, the size-regulating agent is added to the lipid or liposomes before formation of the precipitated cochleate. For example, in one embodiment, the size-regulating agent is introduced into a liposomal suspension from which cochleates will subsequently be formed (e.g., by addition of cation or dialysis). Alternatively, the size-regulating agent may be introduced to a lipid solution, before or after addition of a pharmacologically active agent.

In some embodiments, the cochleates of the present invention can optionally include one or more aggregation inhibitors. The term "aggregation inhibitor," as used herein, refers to an agent that inhibits aggregation of cochleates. The aggregation inhibitor typically is present at least on the surface of the cochleate, and may only be present on the surface of the cochleate (e.g., when the aggregation inhibitor is introduced after cochleate formation). Aggregation inhibitors can be added before, after, or during cochleate formation. A person of ordinary skill in the art will readily be able to determine the amount of aggregation inhibitor needed to form cochleates of the desired size with no more than routine experimentation.

Suitable aggregation inhibitors that can be used in accordance with the present disclosure, include but are not limited to at least one of the following: casein, kappa-casein, milk, albumin, serum albumin, bovine serum albumin, rabbit serum albumin, methylcellulose, ethylcellulose, propylcellulose, hydroxycellulose, hydroxymethyl cellulose, hydroxyethyl cellulose, hydroxypropyl cellulose, hydroxypropylmethyl cellulose, polyvinyl pyrrolidone, carboxymethyl cellulose, carboxyethyl cellulose, pullulan, polyvinyl alcohol, sodium alginate, polyethylene glycol, polyethylene oxide, xanthan gum, tragacanth gum, guar gum, acacia gum, arabic gum, polyacrylic acid, methylmethacrylate copolymer, carboxy polymer, amylose, high amylose starch, hydroxypropylated high amylose starch, dextrin, pectin, chitin, chitosan, levan, elsinan, collagen, gelatin, zein, gluten, carrageenan, carnauba wax, shellac, latex polymers, milk protein isolate, soy protein isolate, whey protein isolate and mixtures thereof.

Any suitable lipid can be used to make the cochleate. In one embodiment, the lipid includes one or more negatively charged lipids. As used herein, the term "negatively charged lipid" includes lipids having a head group bearing a formal negative charge in aqueous solution at an acidic, basic or physiological pH, and also includes lipids having a zwitterionic head group. In one embodiment, the negatively charged lipid is a phospholipid.

The cochleates can also include non-negatively charged lipids (e.g., positive and/or neutral lipids). Typically, the cochleates include a significant amount of negatively charged lipids. In certain embodiments, a majority of the lipid is negatively charged. In one embodiment, the lipid is a mixture of lipids, comprising at least 50% negatively charged lipid, such as a phospholipid. In another embodiment, the lipid includes at least 75% negatively charged lipid, such as a phospholipid. In other embodiments, the lipid includes at least 85%, 90%, 95% or 98% negatively charged lipid, such as a phospholipid. In yet other embodiments, the negatively charged lipid (e.g., phospholipid) comprises between 30%-70%, 35%-70%, 40%-70%, 45%-65%, 45%-70%, 40%-60%, 50%-60%, 45%-55%, 45%-65%, or 45%-50% of the total lipid in the cochleate. In certain embodiments, the negatively charged lipid (e.g., phospholipid) comprises between 40%-60% or 45%-55% of the total lipid in the cochleate. In some embodiments, the negatively charged lipid (e.g., phospholipid) comprises between 30%-70%, 35%-70%, 40%-70%, 45%-65%, 45%-70%, 40%-60%, 50%-60%, 45%-55%, 45%-65%, or 45%-50% of the total lipid in the non-hydrophobic domain component of the cochleate. In certain embodiments, the negatively charged lipid (e.g., phospholipid) comprises between 40%-60% or 45%-55% of the total lipid in the non-hydrophobic domain component of the cochleate. In some embodiments, the negatively charged lipid is a phospholipid and comprises between 30%-70%, 35%-70%, 40%-70%, 45%-65%, 45%-70%, 40%-60%, 50%-60%, 45%-55%, 45%-65%, or 45%-50% of the total phospholipid in the cochleate or in the non-hydrophobic domain component of the cochleate. In some embodiments, the negatively charged lipid is a phospholipid and comprises between 40%-60% or 45%-55% of the total phospholipid in the cochleate or in the non-hydrophobic domain component of the cochleate.

The negatively charged lipid can include egg-based lipids, bovine-based lipids, porcine-based lipids, plant-based lipids or similar lipids derived from other sources, including synthetically produced lipids. The negatively charged lipid can include phosphatidylserine (PS), dioleoylphosphatidylserine (DOPS), phosphatidic acid (PA), phosphatidylinositol (PI), and/or phosphatidyl glycerol (PG) and or a mixture of one or more of these lipids with other lipids. Additionally or alternatively, the lipid can include phosphatidylcholine (PC), phosphatidylethanolamine (PE), diphosphotidylglycerol (DPG), dioleoyl phosphatidic acid (DOPA), distearoyl phosphatidylserine (DSPS), dimyristoyl phosphatidylserine (DMPS), dipalmitoyl phosphatidylglycerol (DPPG) and the like. In another embodiment, the phosphatidylserine is egg or bovine derived phosphatidylserine.

Cochleates Containing Soy Lipids

In some typical embodiments, the cochleates, including the geode cochleates, described herein below, are prepared using legume-based phospholipids, more typically soy-based lipids. Such soy-based lipids can be natural or synthetic. Even more typically, the soy-based lipids are soy phospholipids, such as soy phosphatidylserine is in an amount of 40%-74% by weight of the lipid component of the cochleates. Alternatively, the soy phosphatidylserine can be about 40%, 45%, 50%, 55%, 60%, 65% or 70% or any incremental value thereof, by weight of the lipid component of the cochleates. It is to be understood that all values, and ranges between these values and ranges are meant to be encompassed by the present disclosure. In a typical embodiment, the phospholipid comprises 45-70% soy phosphatidylserine. In a more typical embodiment, the phospholipid comprises 45-55% soy phosphatidylserine.

Soy phosphatidylserine is commercially available, e.g., from Avanti Polar Lipids, Inc. Alabaster, Ala. Alternatively, soy phosphtidylserine can be purified from soy phospholipid compositions, which are mixtures of several soy phospholipids, according to well-known and standard purification techniques.

In some embodiments, neutral lipids are used in combination with the soy phosphatidylserine to make the instant cochleates. As used herein, the term "neutral lipids" include any of a number of lipid species, which exist either in an uncharged or neutral zwitterionic form at physiological pH and, thus, are included within the group of lipids lacking an anionic function. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the cochleate compositions described herein is generally guided by consideration of, e.g., cochleate size and stability. Lipids having a variety of acyl chain groups of varying chain length and degree of saturation are available or may be isolated or synthesized by well-known techniques. In one group of embodiments, lipids containing saturated fatty acids with carbon chain lengths in the range of $C_{14}$ to $C_{22}$ can be used. In another group of embodiments, lipids with mono or di-unsaturated fatty acids with carbon chain lengths in the range of $C_{14}$ to $C_{22}$ can be used. In yet another group of embodiments, lipids with mono or di-unsaturated fatty acids with carbon chain lengths in the range of $C_8$ to $C_{12}$ can be used. Additionally, lipids having mixtures of saturated and unsaturated fatty acid chains can be used.

In some embodiments, the neutral lipids used in the present disclosure are DOPE, DSPC, DPPC, POPC, or any related phosphatidylcholine. The neutral lipids useful in the present disclosure may also be composed of sphingomyelin, dihydrosphingomyeline, or phospholipids with other head groups, such as serine and inositol.

In a typical implementation, 99.9% pure dioleoyl phosphatidylserine, 99.9% pure soy phosphatidylserine, 75% soy phosphatidylserine and 50% soy phosphatidylserine, are used to manufacture cochleates. The lipid composition of 99.9% pure phosphatidylserine is typically modified by the addition of neutral lipids, including, but not limited to sphingomyelin and/or phosphatidylcholine. When lower purity phosphatidylserine (e.g., 50% soy phosphatidylserine) is used as a starting material, the lower purity phosphatidylserine can be subjected to extraction steps to remove unwanted impurities, such as, nucleases.

Geode Cochleates

In some implementations, the cochleate of the present disclosure is a geode cochleate, or a geodate, as described, for example, in U.S. Patent Publication 2013/0224284, the entire disclosure of which is incorporated herein by reference. Geode cochleates further comprise a lipid monolayer comprising a negatively charged phospholipid, where the lipid monolayer surrounds a hydrophobic domain, such as an oil, and a cargo moiety, such as an antifungal compound as described herein, which is dispersed within the hydrophobic domain. The lipid monolayer is sequestered within the lipid strata of the geode cochleate.

As used herein, a "hydrophobic domain" is a composition that is sufficiently hydrophobic in nature to allow formation of a lipid monolayer about its periphery. A hydrophobic domain typically includes a hydrophobic composition, such as oil or fat, associated with a cargo moiety, such as an antifungal compound of the disclosure, such as AmB. In certain embodiments, the ratio between the hydrophobic domain (HD) and the phospholipid component of the geode cochleate (PPLGD) HD:PPLGD or the castor oil domain (COD) and phospholipid component of the geode cochleate (PPLGD) COD:PPLGD is 1:20 or less, 1:15 or less, 1:10 or less, 1:8 or less, 1:6 or less, 1:5 or less, 1:4 or less, 1:3.5 or less, 1:3 or less, 1:2.75 or less, 1:2.5 or less, 1:2.25 or less, 1:2 or less, 1:1.75 or less, 1:1.5 or less, 1:1.25 or less 1:1 or less.

Figure 5:
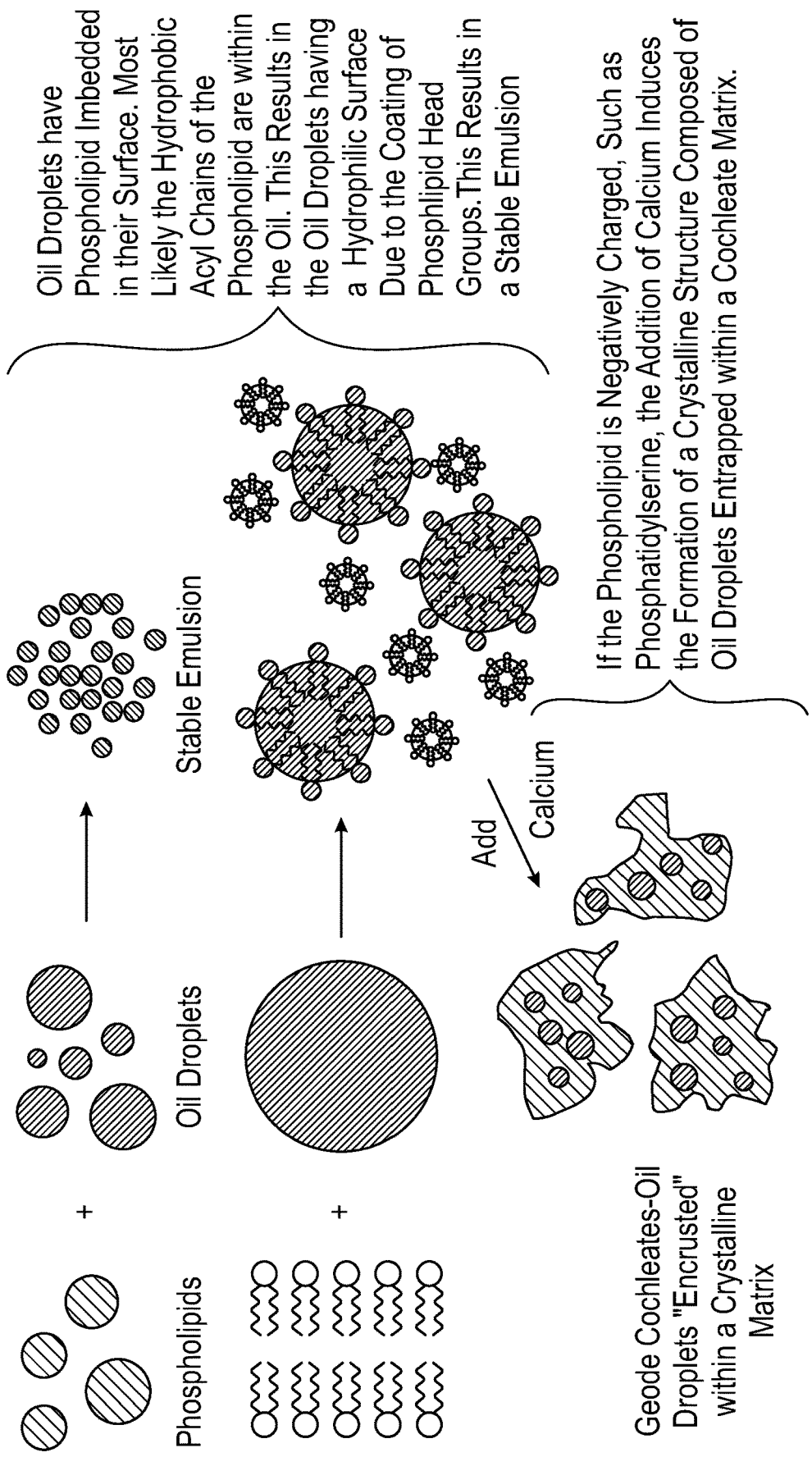
FIG. 5 depicts an exemplary preparation of geode cochleates as described in the detailed description.

FIG. 5 shows an exemplary schematic of how geode cochleates can be made. In this exemplary method, a phospholipid (represented as an open ring) is combined with a hydrophobic domain (shaded circles), such as an oil, and mixed to form a stable emulsion comprising liposomes and lipid monolayers surrounding the hydrophobic domain. A cargo moiety, such as an antifungal compound, etc., may be dispersed within the hydrophobic domain. The hydrophobic domains have phospholipids imbedded in their surface. Without intending to be bound by any theory, it is believed that the hydrophobic acyl chains of the phospholipid are within the hydrophobic domains, resulting in the hydrophobic domains having a hydrophilic surface due to the coating of the phospholipid head groups and forming a stable emulsion. If the phospholipid is negatively charged, such as with phosphatidylserine, the addition of a divalent cation, such as calcium, induces the formation of a crystalline structure (or lipid strata) comprising alternating divalent cations and phospholipid bilayers. The lipid strata are represented with hatching. In a geode cochleate, the lipid monolayers surrounding the hydrophobic domain are "encrusted" or "entrapped" within the crystalline matrix, akin to a "geode."

Pharmaceutical Compositions

The cochleate composition as described herein can be prepared as a pharmaceutical composition. Suitable preparation forms for the pharmaceutical compositions disclosed herein include, for example, tablets, capsules, soft capsules, granules, powders, suspensions, emulsions, microemulsions, nanoemulsions, unit dosage forms, rings, films, suppositories, solutions, creams, syrups, transdermal patches, ointments and gels. Typically, however, the cochleates are prepared for mucosal, e.g., oral or intranasal, typically oral administration.

The pharmaceutical compositions can include other pharmaceutically acceptable excipients, such as a buffer (e.g., Tris-HCl, acetate, phosphate) of various pH and ionic strength; an additive such as albumin or gelatin to prevent absorption to surfaces; a protease inhibitor; a permeation enhancer; a solubilizing agent (e.g., glycerol, polyethylene glycerol); an anti-oxidant (e.g., ascorbic acid, sodium metabisulfite, butylated hydroxyanisole); a stabilizer (e.g., hydroxypropyl cellulose, hydroxypropylmethyl cellulose); a viscosity increasing agent (e.g., carbomer, colloidal silicon dioxide, ethyl cellulose, guar gum); a sweetener (e.g. aspartame, citric acid); a preservative (e.g., Thimerosal, benzyl alcohol, parabens); a flow-aid (e.g., colloidal silicon dioxide), a plasticizer (e.g., diethyl phthalate, triethyl citrate); an emulsifier (e.g., carbomer, hydroxypropyl cellulose, sodium lauryl sulfate); a polymer coating (e.g., poloxamers or poloxamines, hypromellose acetate succinate); a coating and film forming agent (e.g., ethyl cellulose, acrylates, polymethacrylates, hypromellose acetate succinate); an adjuvant; a pharmaceutically acceptable carrier for liquid formulations, such as an aqueous (water, alcoholic/aqueous solution, emulsion or suspension, including saline and buffered media) or non-aqueous (e.g., propylene glycol, polyethylene glycol, and injectable organic esters such as ethyl oleate) solution, suspension, emulsion or oil; and a parenteral vehicle (for subcutaneous, intravenous, intraarterial, intrathecal or intramuscular injection), including but not limited to, sodium chloride solution, Ringer's dextrose, dextrose and sodium chloride, lactated Ringer's and fixed oils.

In certain embodiments, the pharmaceutical composition comprises a salt, such as NaCl or a bile salt, such as oxycholate, cholate, chenodeoxycholate, taurocholate, glycocholate, taurochenodeoxycholate, glycochenodeoxycholate, deoxycholate or lithocholate. Bile salts are bile acids compounded with a cation, usually sodium. Bile acids are steroid acids found predominantly in the bile of mammals and are commercially available. In one embodiment, the bile salts comprise cholate. In another embodiment, the bile salts comprises deoxycholate. In yet another embodiment, the bile salts comprise cholate and deoxycholate. In another embodiment, the bile salts consist of cholate and deoxycholate.

In certain embodiments, the concentration of NaCl is 1 mM to 1M, 1 mM to 0.5M, 1 mM to 0.1M, 1 mM to 50 mM, 10 mM to 100 mM, 10 mM to 50 mM, 0.1M to 1M, 0.1M to 0.5M, or 0.5M to 1M. In certain embodiments, the concentration of the bile salts is 1 mM to 100 mM, 1 mM to 50 mM, 1 mM to 25 mM, 1 mM to 10 mM, 1 mM to 5 mM, 0.1 mM to 5 mM, 0.1 mM to 1 mM, or 0.1 mM to 0.5 mM bile salts.

These excipients are provided by way of example and it will be known to those of skill in the art that there will be other or different excipients that can provide the same chemical features as those listed herein.

Dosage and Administration

A pharmaceutical composition comprising a cochleate composition, as disclosed herein, is formulated to be compatible with its intended route of administration. Methods to accomplish the administration are known to those of ordinary skill in the art. This includes, for example, injections, by parenteral routes such as intrathecal, intravenous, intravascular, intraarterial, subcutaneous, intramuscular, intraperitoneal, intraventricular, intraepidural, or others as well as oral, nasal, ophthalmic, rectal, or topical. Typically, the cochleate is administered intranasally, for example, by administering a suspension, or orally, for example, by administering a suspension, a tablet, a capsule, a softgel or other oral dosage form.

In certain embodiments, the antifungal (e.g., encochleated amphotericin B, unencochleated 5-FC and/or unencochleated fluconazole) is administered at a dosage of between 0.1-20 mg/kg, 5-10 mg/kg, 5-15 mg/kg, 10-15 mg/kg, 10-13 mg/kg, 10-20 mg/kg, 5-25 mg/kg, 1-30 mg/kg or 2.5 mg/kg. For example, encochleated amphotericin B may be administered in an amount ranging from 0.1 mg/kg to 10 mg/kg, such as 1 mg/kg. Alternatively, the antifungal can be administered at a fixed dosage of about 200-1000 mg/day, 400-1000 mg/day, 200-800 mg/day, 300-800 mg/day, 400-800 mg/day, 500-700 mg/day, 200-2000 mg/day, 100-4000 mg/day, 100-600 mg/day, 200-600 mg/day, 400-600 mg/day, or 300-700 mg/day, including, but not limited to about 400, 500, 600, 700, 800, 900, 1000, 1500, 2000, 2500, 3000, 3500, or 4000 mg. For example, encochleated amphotericin B may be administered in an amount ranging from 0.1 mg/kg/day to 4 mg/kg/day, such as 0.2, 0.4, 0.6, 0.8, 1.0, 1.2, 1.4, 1.6, 2, 3, 4 mg/kg/day for a period of two weeks. Due to lower toxicity, the encochleated antifungal may be administered more frequently or for a longer duration than an intravenously administered antifungal. In certain embodiments, the encochleated antifungal may be administered once per day, twice per day, three times per day, or four times per day. In another embodiment, the cochleate formulation is administered once per week, twice per week, three times per week, or four times per week. In one embodiment, the encochleated antifungal may be administered 2-3 times weekly. In other embodiments, the cochleate formulation is administered daily for at least 1, 2, 3, 4, 5, 6, 7, 8, 9, 10, 11, or 12 weeks. In another embodiment, the cochleate formulation is administered daily for at least 3 months, at least 4 months, or at least 6 months. Typically, the cochleate composition is administered for two weeks.

Methods of Treatment

One aspect of the present disclosure is directed to a method of treating or preventing an infection in a subject due to a *Cryptococcus* spp., which method comprises: administering to a subject in need thereof a formulation comprising a cochleate composition, wherein the cochleate composition comprises at least two antifungal compounds, wherein the at least two antifungal compounds are selected from amphotericin B, 5-Flucytosine, fluconazole, ketoconazole, ravuconazole, albaconazole, itraconazole, posaconazole, isavuconazole and/or voriconazole, wherein at least one of the at least two antifungal compounds is formulated as a cochleate.

The cochleates used in the instant methods may be prepared using the lipids and methods as described herein. In some embodiments, the at least two antifungal compounds are formulated in the same cochleate. In other embodiments, the at least two antifungal compounds are formulated in a different cochleate. Typically, the at least two antifungal compounds are amphotericin B and 5-Flucytosine and the amphotericin B is formulated as a cochleate.

In some embodiments, the infection involves skin, lung, prostate, bone and/or the central nervous system (CNS). Typically, the infection involves the CNS, such as the meninges. In some embodiments, the infection is cryptococcal meningeoencephalitis or cryptococcal meningitis. In some embodiments, the infection, which is caused by a *Cryptococcus* spp., is caused by *Cryptococcus neoformans*. In other embodiments, the infection is caused by *Cryptococcus gattii*.

The administration may be oral, intranasal, intrathecal or intravenous. However, most typically, the administration is oral. In some embodiments, the cochleate composition is administered daily for at least 7 days, at least 14 days, at least 21 days, or at least 28 days.

In some embodiments, the antifungal compounds of the cochleate composition are delivered to the brain. In some embodiments, the antifungal compounds of the cochleate composition are delivered to the brain after oral administration. In some embodiments, the cochleate composition of the present disclosure has the ability to reduce fungal colony forming units (CFU's) by at least 5%, such as at least 8%. More preferably, AmB cochleates can reduce CFU's in the brain, for example, by least 10%, such as at least 25% and even more preferably by 50%, 75%, 85%, 95%, 96%, 97%, 98%, 99%, 99.5%, 99.9%, or 100%. All individual values and ranges falling between these ranges and values are within the scope of the present invention. Reduction in colony forming units may be in vivo or in vitro.

As used herein, the term "subject" refers to any animal including, without limitation, a human, a mouse, a rat, a rabbit, a non-human primate, or any other mammal. In one embodiment, the subject is a primate. In another embodiment, the subject is a human.

In some embodiments, the subject is an immunocompromised subject. For example, the subject may have HIV/

AIDS, lymphoma, cirrhosis of the liver or the subject may have received an organ transplant. In other embodiments, the subject is an immunocompetent individual.

The present disclosure also provides a method of treating or preventing an infection due to a *Cryptococcus* spp., as described herein, which method comprises: administering to a subject in need thereof a formulation comprising a cochleate, as described herein, wherein the cochleate comprises an antifungal compound, wherein the antifungal compound is selected from at least one of 5-Flucytosine, fluconazole, ketoconazole, ravuconazole, albaconazole, itraconazole, posaconazole, isavuconazole and/or voriconazole.

Other contemplated anti-fungal compounds for use in the instant methods include those capable of inhibiting the synthesis of a cell wall component, such as glycosylphosphatidylinositol (GPI)-anchored mannoproteins, e.g., E1210. In other embodiments, the anti-fungal compound for use in the methods is an ergosterol synthesis inhibitor, such as VT-1129, which is orally available, shows good CNS penetration and is fungicidal in mouse models of *Cryptococcus* spp. infection.

In other embodiments, the anti-fungal compound is an orally available compound, which is known to exhibit an additive or synergistic activity with fluconazole against *Cryptococcus* spp. Such anti-fungal compounds include amiodarone (a cardiac anti-arrhythmic drug) phenothiazine (an antipsychotic) and taxmoxifen (an estrogen antagonist).

As used herein, "preventing" an infection due to a *Cryptococcus* spp., comprises preventing a recurrence of infection. In some embodiments for preventing a recurrence of infection, the present cochleate composition does not contain AmB. In some embodiments, preventing an infection due to a *Cryptococcus* spp., comprises treating a mammal or human which/who is positive for a cryptococcal species antigen (using, for example, an IMMY Inc. (Norman, Okla.) cryptococcal antigen test).

Toxicity

Oral administration of encochleated antifungals, such as AmB, exhibit reduced toxicity as compared to parenteral administration of unencochleated antifungals. Subjects treated with parenteral, unencochleated antifungals, such as AmB must be under close clinical observation because of the potential, e.g, for nephrotoxicity, which is associated with their use.

Administering antifungal agents, such as AmB, as part of a cochleate formulation reduces the toxicity associated with this antifungal and permits the administration of higher doses of AmB. The lower toxicity for encochleated antifungals such as AmB, permits such antifungals to be delivered orally at lower doses with improved efficacy and reduced toxicity. Alternatively, due to the lower toxicity, the encochleated antifungals can be administered more frequently and/or at higher doses with less risk of adverse consequences.

EXAMPLES

Example 1. Materials and Methods

Antifungals

Formulations of encochleated Amphotericin B (CAMB) (alone or in combination with 5-Flucytosine or Fluconazole) and routes of administration were evaluated and compared to FUNGIZONE® to assess which treatment was most efficient against clearing *C. neoformans* in mice as measured by survival after cryptococcal inoculation. The evaluated formulations, dosages and routes of administration are described in Tables 1-3, below.

CAMB was prepared using good manufacturing practice (GMP) as described in U. S. Publication No. 2014/0220108 and FIG. 4. Additional CAMB formulations were evaluated, which were also manufactured according to GMP, including those subjected to soniciation after liposome formation to further reduce cochleate size as described herein above, as well as formulations that were modified during cochleate preparation to include aggregation inhibitors (bovine serum albumin or light cream and milk) or size selecting agents (e.g., deoxycholate). Other evaluated CAMB GMP formulations included those containing cochleates prepared using a ratio of lipid to amphotericin B of 2.5:1 instead of 10:1. See Tables 2 and 3.

5-Flucytosine (5-FC), $C_4H_4FN_3O$, (Sigma Aldrich, Inc. St. Louis, Mo.) and FUNGIZONE® (Amphotericin B deoxycholate, provided by the National Institutes of Health Department of Veterinary Resources, Bethesda, Md.) were reconstituted according to the manufacturers' instructions and diluted in sterile water. FUNGIZONE® was replaced every week during the study with a new reconstituted vial and was refrigerated after every use. Fluconazole (99%), $C_{13}H_{12}F_2N_6O$, was obtained from Alfa Aesar, Thermo-Fisher Scientific, Inc., Ward Hill, Mass.

Infectious Strain and Culture Conditions.

Mice were inoculated with *C. neoformans*, strain H99/ATCC 208821, (American Type Culture Collection, Rockville, Md.), which was prepared as follows. Cells from a *C. neoformans* suspension were streaked onto yeast extract peptone dextrose (YPD) agar plates, which were then incubated at 37° C. for 48 hours. A well-separated colony was resuspended in 25 milliliters YPD broth containing chloramphenicol and incubated in a flask on a shaking incubator at 37° C. overnight. The cells were recovered by centrifugation at 4,000 rpm for 5 minutes and washed two times in phosphate-buffered saline (PBS) by resuspension and centrifugation. Challenge organisms were quantified by hemocytometry and were diluted with PBS to a final concentration of $10^5$ organisms per milliliter. The viable count was confirmed by serially diluting the *C. neoformans* suspension and plating the inoculum onto YPD agar plates.

Infection with *C. neoformans* was induced by injection of $10^4$ H99 cells in 0.1 milliliter of PBS via the lateral tail vein after recordation of initial body weight. Systemic infections were produced that caused complete mortality in nontreated control groups within 14 to 24 days. Female Hsd:ND4 Swiss Webster Outbred mice (age, 9 to 10 weeks; weight, 20 to 29 grams) (Harlan Laboratories, Frederick, Md. (Now Envigo, Inc.) were used throughout the experiments. The mice had been allowed to acclimate to the facility for a week prior to infection and were maintained in microisolator cages.

Three different treatment trials were performed. In the first trial, infected mice were treated with 50 milligram per kilogram per day (mg/kg/day) CAMB by oral gavage (PO) or 5 mg/kg/day FUNGIZONE® by intraperitoneal (IP) injection (Table 1). 5 mice were used per treatment group. Agent administration began 24 hours following infection and continued once daily following body weight measurements for 28 consecutive days. A group of 5 infected, untreated mice was used as a control.

In the second trial, infected mice were treated with 10 mg/kg/day, 25 mg/kg/day or 50 mg/kg/day CAMB by PO, IP or subcutaneous injection (SQ). The CAMB was administered either alone or in combination with 5-Flucytosine. In addition, infected mice were treated with 5-Flucytosine alone or 5 mg/kg/day FUNGIZONE® alone, each administered by IP injection (Table 2). As in the first trial, 5 mice were also used per treatment group and a group of 5 infected, untreated mice was used as a control. For indicated groups, 250 mg of 5-Flucytosine/250 milliliters of sterilized water was prepared every three days, aliquoted into clean, autoclaved water bottles and placed in the cages of the two groups of mice. Agent administration began 72 hours following infection and continued once daily following body weight measurements for 28 consecutive days.

In the third trial, infected mice were treated with 5 mg/kg/dose, 25 mg/kg/dose or 50 mg/kg/dose CAMB by PO or IP injection either alone or in combination with 5-Flucytosine or fluconazole. Mice were also dosed with 5-Flucytosine alone, fluconazole alone or a 5 mg/kg/dose of FUNGIZONE® by IP injection either alone or in combination with 5-Flucytosine (Table 3). Animals were dosed once or twice daily as stated in Table 3 following daily body weight measurements. 5 mice were used per treatment group and a group of 5 infected, untreated mice was used as a control. For indicated groups, 250 mg of 5-Flucytosine/250 ml of sterilized water was prepared every three days, aliquoted into clean, autoclaved water bottles and placed in the cages of the four groups of mice. Fluconazole, where indicated, was dosed either alone or in combination at 25 mg/kg/day in two doses by oral gavage. Agent administration began 72 hours following infection and continued once daily for 28 consecutive days.

Survival and brain studies for each of the three trials were used to determine antifungal efficacy. Mortality was recorded throughout each of the three trials. The animals were necropsied at death and the brain was removed aseptically, weighed, and homogenized in 1 milliliter sterile water. The microbiological response to antifungal treatment was evaluated by concentration (in CFU per gram) of *C. neoformans* in brain tissue. Serial dilutions using sterile PBS of homogenized brain were plated in duplicate onto YPD agar plates. Culture plates were incubated at 37° C. for 48 hours, after which the CFU were counted and the number of CFU per gram of brain tissue was calculated. The method was sensitive for detection of >10 CFU/g. The culture-negative plates were counted as having 0 CFU/g.

Example 2. Results

Trial 1

Figure 6:
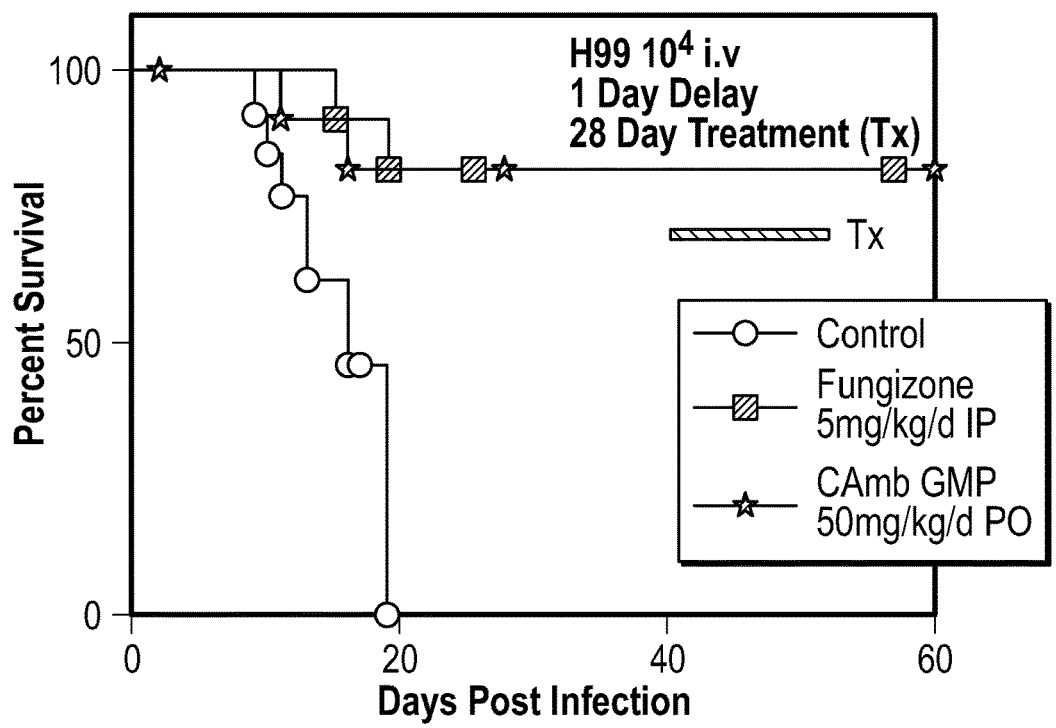
FIG. 6 depicts in vivo efficacy results of *C. neoformans*-infected mice, treated with either CAMB or FUNGIZONE® as described in Example 2.

Mice were infected with $1\times10^4$ CFU intravenously with *C. neoformans* strain H99 and after 1 day began daily therapy for 28 days, as noted above and as indicated in FIG. 6, then followed for sixty days. FIG. 6 shows the percent survival for each group at the indicated times. As is evident from FIG. 6, CAMB, used alone after 1 day of an infection incubation period, resulted in 80% survival of mice out to 60 days, which was equivalent to amphotericin B deoxycholate injection (FUNGIZONE®) and superior to an untreated control group, which showed 100% mortality at day 20.

Trial 2

Figure 7:
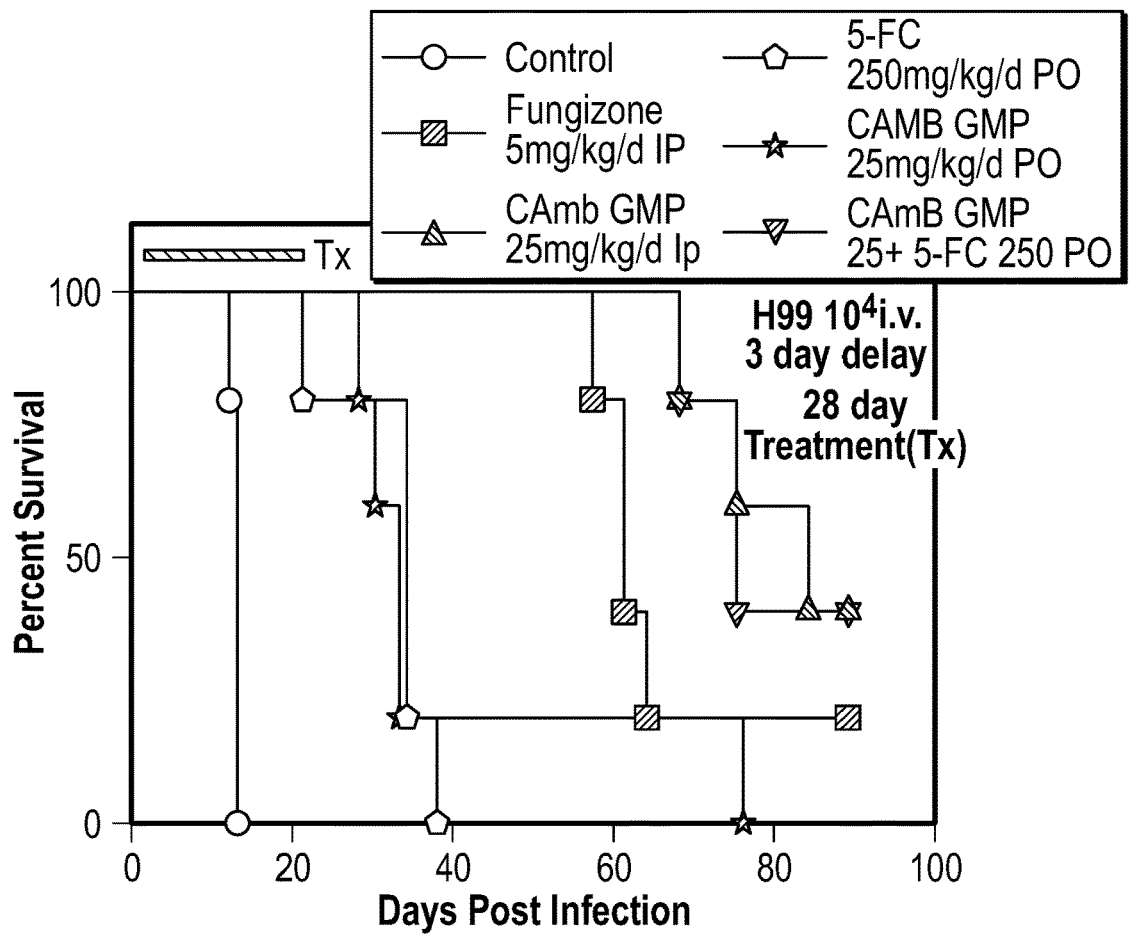
FIG. 7 depicts in vivo efficacy results of *C. neoformans*-infected mice treated with CAMB, FUNGIZONE® and/or 5-Flucytosine as described in Example 2.

Mice were intravenously infected with $1\times10^4$ colony forming units of *C. neoformans* strain H99. After 3 days, daily therapy began for 28 days as noted above and as indicated in Table 4 and FIG. 7. The mice were followed until moribund and then sacrificed. The experiment was terminated at 188 days with 1 mouse alive from Group No. 1. Table 4 shows the percent survival for Groups 1-11. FIG. 7 depicts the percent survival for Groups 1, 2 and 4-6 only. As shown in Table 4, median survival of the untreated mice was 13 days, which was extended by treatment with FUNGIZONE® IP 5 mg/kg/day (61 days, p=0.004) or by CAMB administered by any of the PO, SQ or IP routes (33, 50, 84 days, p=0.004). However, survival using CAMB was improved by either using the IP route (84 days, p=0.022), or by addition of oral 5-FC in the drinking water (75 days, p<0.05).

*C. neoformans*-related brain death was validated by the presence of swollen heads at the time of death and by culturing the homogenized brains of the mouse carcasses and subsequently obtaining colonies from the YPD plates (see Table 5). The one mouse alive from Group 1 on culture contained 225 CFU of *C. neoformans*, indicative of partial treatment by FUNGIZONE® IP.

Based on the survival rate analysis of the eleven groups of compounds tested, the mice in Groups 1, 2 and 6 survived the longest, more than 60 days past the end of treatment. It can be concluded that Group 1 (FUNGIZONE® IP injection), Group 2 (CAMB IP injection) and Group 6 (CAMB PO+5-Flucytosine in drinking water), provided the mice with better rates of survival against *C. neoformans* than the other treated groups. For oral treatment, the addition of 5-FC significantly prolonged survival over treatment with encochleated amphotericin B alone and was roughly equivalent to that of FUNGIZONE® IP.

Trial 3

Figure 8:
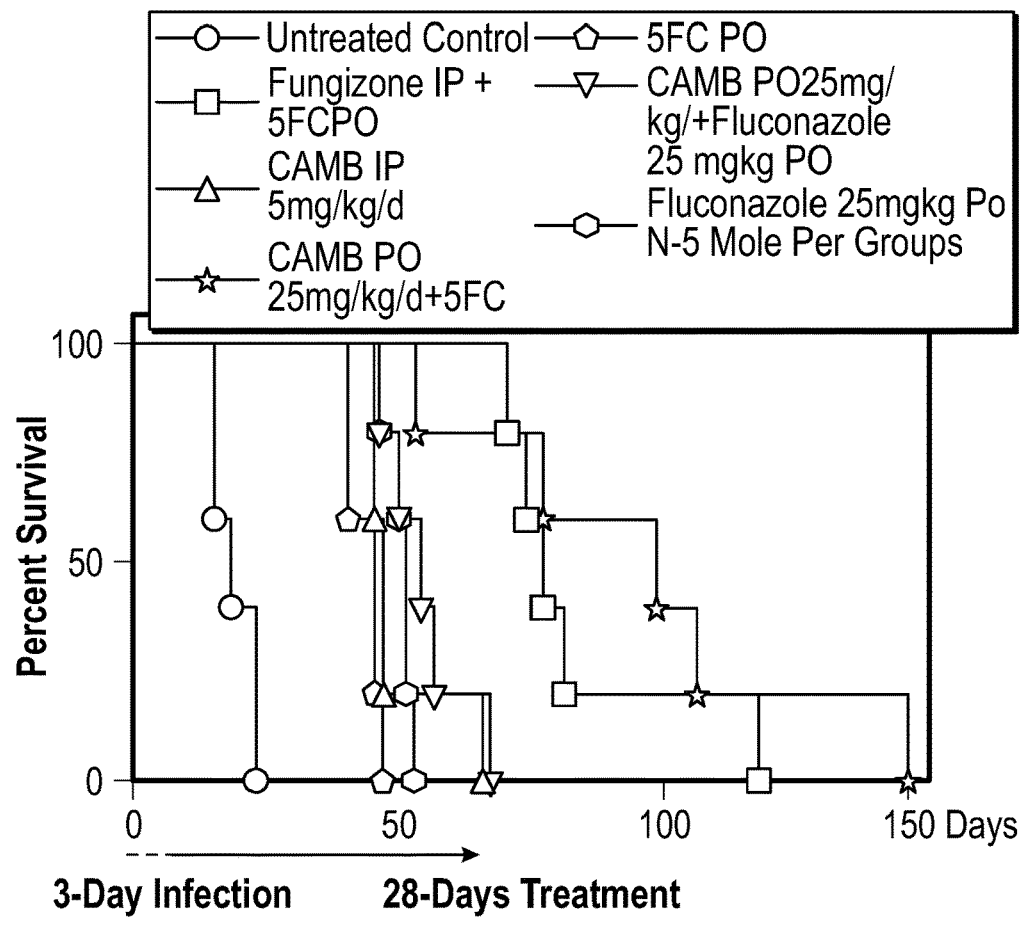
FIG. 8 depicts in vivo efficacy results of *C. neoformans*-infected mice treated with CAMB, FUNGIZONE®, 5-FC and/or fluconazole as described in Example 2.

Mice were intravenously infected with $1\times10^4$ CFU of *C. neoformans* strain H99. After 3 days, daily therapy began for 28 days as noted above and as indicated in Table 6 and FIG. 8. The mice were followed until moribund and then sacrificed. Table 6 shows the percent survival for Groups 1-11. FIG. 8 depicts the percent survival for Groups 1, 2, 6, 8, and 9 only. As shown in Table 6, median survival of the untreated mice was 19 days, which was extended by treatment with FUNGIZONE® IP 5 mg/kg/day+5-FC (80 days, p=0.003) or by CAMB, administered daily by either the PO or IP route (35 or 49 days, respectively; p=0.003). Twice daily dosing resulted in a trend towards less survival, which may have been due to repeated trauma, leading to reduced PO intake or CAMB gastrointestinal toxicity (31 days vs. 35 days, p=not statistically significant (NS)). Survival with the oral CAMB preparation was improved by addition of either oral 5-FC in the drinking water (102 days, p=0.002 vs. oral CAMB alone) or by addition of oral fluconazole, although not to as great an extent (56 days, p=0.002).

Figure 9:
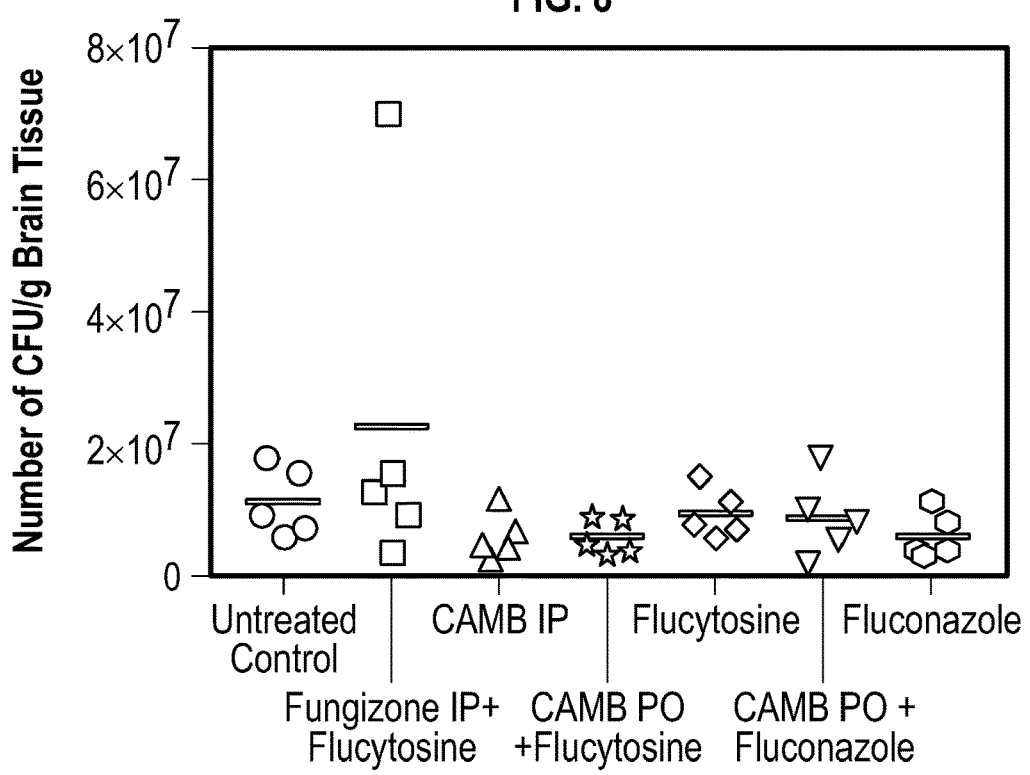
FIG. 9 depicts the number of Colony Forming Units (CFUs) per gram of brain tissue observed for mice treated with CAMB, FUNGIZONE®, 5-FC, fluconazole and combinations thereof as described in Example 2.

The experiment was terminated at 151 days with one mouse alive from Group 6, the CAMB+5-FC group. *C. neoformans*-related brain death was validated by the presence of swollen heads at the time of death and by culturing the homogenized brains obtained from mouse carcasses and subsequently obtaining colonies from the YPD plates. See Table 7 and FIG. 9 for Number of CFU/g Brain Tissue.

Example 3. Brain Localization of Fluorescent Cochleates after Oral Dosing

Figure 10:
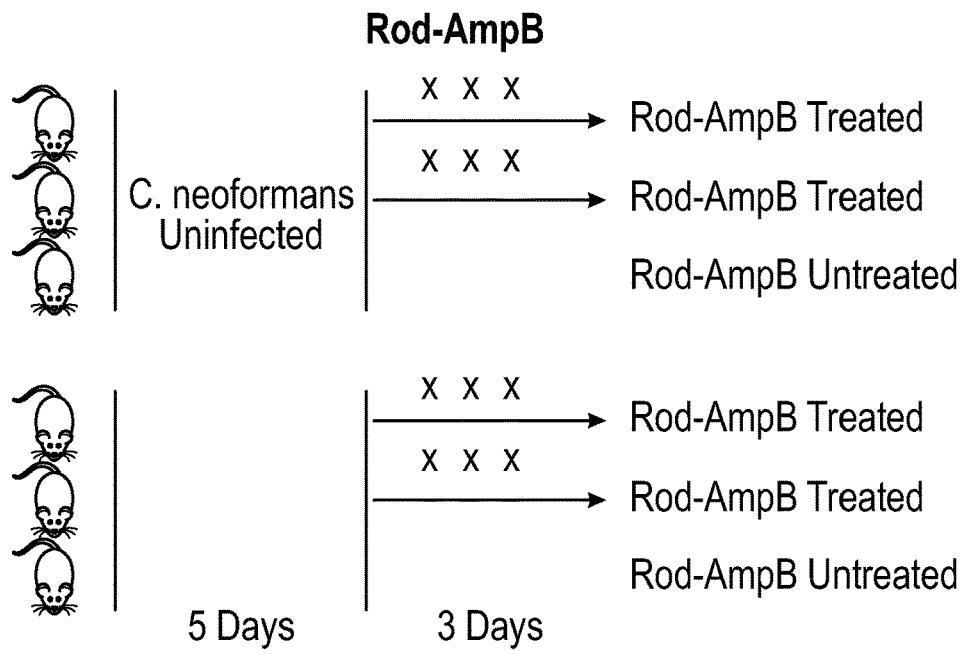
FIG. 10 depicts the study design, which was used to demonstrate that encochleated amphotericin B localizes to the brain after oral dosing as described in Example 3.

In order to determine whether CAMB is actually delivered to brain tissue, three mice were infected by tail vein with $10^4$ *C. neoformans*, strain H99 and three remained uninfected. 5-days later, two mice from each group were treated once daily for 3-days by oral gavage with rhodamine-labeled CAMB (Rod-AmpB) equivalent at 10 mg/kg/day. (See FIG. 10 for schematic of Study Design.) Mice were sacrificed at day 7 and brain material was recovered, homogenized and subjected to microscopy using Differential Interference Contract (DIC) and observed for fluorescence (RFP).

Figure 11:
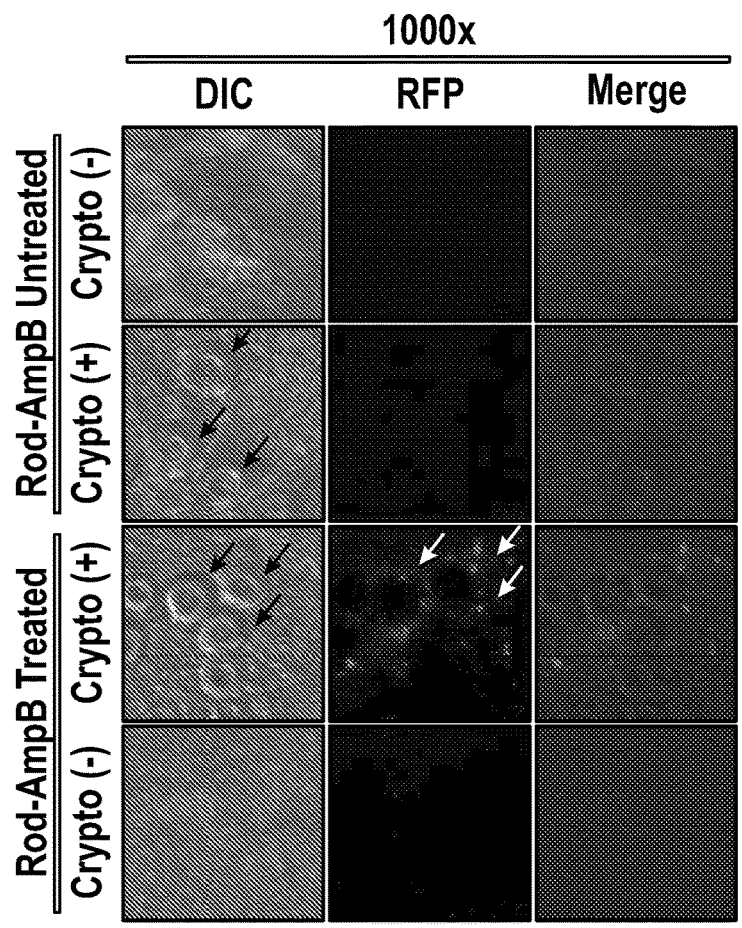
FIG. 11 depicts the delivery of fluorescently-labeled CAMB particles into the brains of mice infected with *C. neoformans* as described in Example 3.

FIG. 11 depicts the results of the study. As shown in FIG. 11, fluorescent imaging demonstrated numerous fluorescent particles in the brains of mice treated with CAMB oral preparations. Increased delivery was evident in brains of infected versus uninfected mice. See FIG. 11. Black arrows depict *C. neoformans* encapsulated organisms and white arrows depict cochleate fluorescence (bar=10 millimeters). Accordingly, the present studies demonstrate that CAMB is delivered to the brain in mice infected with *C. neoformans* and may be used as an effective oral anti-fungal agent in combination with 5-FC, which is equivalent to systemic FUNGIZONE®+5-FC, to treat *C. neoformans* infections.

TABLE 1

Trial 1 Dosing Groups and Routes of Administration

| Group No. | Treatment | Route of Administration | Dose/mg/kg/day |
|---|---|---|---|
|  | No Treatment | Not applicable | Not applicable |
| 1 | FUNGIZONE ® (amphotericin B deoxycholate) | IP | 5 |
| 2 | CAMB | PO | 50 |

TABLE 2

Trial 2 Dosing Groups and Routes of Administration

| Group No. | Treatment | Route of Administration | Dose/mg/kg/day |
|---|---|---|---|
|  | No Treatment | Not applicable | Not applicable |
| 1 | FUNGIZONE ® | IP | 5 |
| 2 | CAMB | IP | 10 |
| 3 | CAMB | SQ | 10 |
| 4 | 5-Flucytosine (5-FC) | oral | 250 in drinking water |
| 5 | CAMB | PO | 25 |
| 6 | CAMB + 5-FC | PO, oral | 25 + 250 in drinking water |
| 7 | CAMB-S | PO | 25 |
| 8 | CAMB-S-Deoxycholate | PO | 25 |
| 9 | CAMB-S-BSA | PO | 25 |
| 10 | CAMB-S-FAT | PO | 25 |
| 11 | CAMB 2.5:1-S | PO | 25 |

S = sonicated,
BSA = bovine serum albumin,
FAT = 50/50 light cream and milk,
IP = intraperitoneal,
SQ = subcutaneous,
PO = oral gavage

TABLE 3

Trial 3 Dosing Groups and Routes of Administration

| Group No. | Treatment | Route of Administration | CAMB Dose (mg/kg) | CAMB regimen | CAMB Daily Dose (mg/kg) | Other Regimen | Other Daily Dose (mg/kg) |
|---|---|---|---|---|---|---|---|
|  | No Treatment | N/A | N/A | N/A | N/A | N/A | N/A |
| 1 | FUNGIZONE ® + 5-FC | IP | N/A | N/A | N/A | QD[2]; Water | 5; 250 |
| 2 | CAMB | IP | 5 | QD | 5 | N/A | N/A |
| 3 | CAMB USPS[1] | PO | 25 | BID[3] | 50 | N/A | N/A |
| 4 | CAMB | PO | 25 | QD | 25 | N/A | N/A |
| 5 | CAMB | PO | 25 | BID | 50 | N/A | N/A |
| 6 | CAMB + 5-FC | PO | 25 | QD | 25 | Water | 250 |
| 7 | CAMB + 5-FC | PO | 25 | BID | 50 | Water | 250 |
| 8 | 5-FC | PO | N/A | N/A | N/A | Water | 250 |
| 9 | CAMB + Fluconazole | PO | 25 | QD | 25 | PO; BID | 25 |
| 10 | CAMB + Fluconazole | PO | 25 | BID | 50 | PO; BID | 25 |
| 11 | Fluconazole | PO | N/A | N/A | N/A | PO; BID | 25 |

[1]Ultra Small Particle Size
[2]Once daily
[3]twice daily

TABLE 4

Median survival of groups from Table 2

| Group No. and Treatment | mg/kg/day | Median survival | vs. Control* | vs. FUNGIZONE ®* | vs. CAMB PO* |
|---|---|---|---|---|---|
| No Treatment Control | N/A | 13 |  |  |  |
| 1. FUNGIZONE ® IP | 5 | 61 | 0.004 |  |  |
| 2. CAMB IP | 10 | 84 | 0.004 | NS** | 0.022 |
| 3. CAMB SQ | 10 | 50 | 0.004 | NS** | NS** |
| 4. 5-Flucytosine (5-FC) Oral | 250 | 34 | 0.004 | 0.002 |  |
| 5. CAMB PO | 25 | 33 | 0.004 | NS** |  |
| 6. CAMB PO + 5-FC Oral | 25, 250 | 75 | 0.004 | NS** | 0.049 |
| 7. CAMB-S PO | 25 | 34 |  |  |  |
| 8. CAMB S-Deoxycholate PO | 25 | 34 |  |  |  |
| 9. CAMB-S-BSA PO | 25 | 33 |  |  |  |

TABLE 4-continued

Median survival of groups from Table 2

| Group No. and Treatment | mg/kg/day | Median survival | vs. Control* | vs. FUNGIZONE ®* | vs. CAMB PO* |
|---|---|---|---|---|---|
| 10. CAMB-S-FAT PO | 25 | 34 | | | |
| 11. CAMB 2.5:1-S PO | 25 | 38 | | | |

*N = 5 mice per group; log rank (Mantel-Cox, univariate)

**NS = not statistically significant

TABLE 5

Number of CFU/g of Brain (Groups from Table 2)

| Group No. and Treatment | Mouse 1 | Mouse 2 | Mouse 3 | Mouse 4 | Mouse 5 |
|---|---|---|---|---|---|
| No Treatment Control | 3,600,000 | 3,000,000 | 8,700,000 | 7,900,000 | 6,700,000 |
| 1. FUNGIZONE ® IP | 4,100,000 | 4,200,000 | 12,000,000 | 6,700,000 | 0 |
| 2. CAMB IP | 3,700,000 | 8,700,000 | 1,500,000 | 1,000,000 | 10,000,000 |
| 3. CAMB SQ | 12,500,000 | 8,700,000 | 8,200,000 | 2,100,000 | 2,500,000 |
| 4. 5-Flucytosine (5-FC) Oral | 1,700,000 | 5,100,000 | 17,400,000 | 8,300,000 | 3,200,000 |
| 5. CAMB PO | 5,900,000 | 10,700,000 | 5,100,000 | 2,600,000 | 6,700,000 |
| 6. CAMB PO + 5-FC Oral | 6,000,000 | 4,300,000 | 7,300,000 | 720,000 | 14,000,000 |
| 7. CAMB-S PO | 4,100,000 | 5,100,000 | 9,400,000 | 2,900,000 | 10,300,000 |
| 8. CAMB S-Deoxycholate PO | 3,000,000 | 18,400,000 | 9,000,000 | 3,100,000 | 2,700,000 |
| 9. CAMB-S-BSA PO | 18,200,000 | 11,500,000 | 11,100,000 | 4,400,000 | 10,700,000 |
| 10. CAMB-S-FAT PO | 25,200,000 | 8,600,000 | 2,000,000 | 72,000,000 | 5,000,000 |
| 11. CAMB 2.5:1-S PO | 19,200,000 | 7,000,000 | 3,800,000 | 3,000,000 | 5,000,000 |

TABLE 6

Median survival of groups from Table 3

| Group, Treatment, Frequency and Route of Administration | Dosage (mg/kg/day) | Median survival (days) | vs. Control* | vs. FUNGIZONE ® + 5-FC* | vs. CAMB PO daily* |
|---|---|---|---|---|---|
| No Treatment | N/A | 19 | N/A | | |
| 1. FUNGIZONE ® IP + 5-FC Oral | 5 | 80 | 0.003 | | |
| 2. CAMB IP QD | 5 | 49 | 0.003 | 0.002 | 0.01 |
| 3. CAMB USPS[1] PO BID | 50 | 42 | 0.003 | 0.003 | NS** |
| 4. CAMB PO, QD | 25 | 35 | 0.003 | 0.002 | |
| 5. CAMB PO, BID | 50 | 31 | 0.025 | 0.002 | |
| 6. CAMB PO, QD + 5-FC oral | 25, 250 | 102 | 0.003 | NS** | 0.002 |
| 7. CAMB PO BID + 5-FC oral | 50, 250 | 62 | 0.043 | 0.016 | |
| 8. 5-FC oral | 250 | 47 | 0.003 | 0.002 | |
| 9. CAMB PO QD + Fluconazole PO BID | 25, 25 | 56 | 0.003 | 0.002 | 0.002 |
| 10. CAMB PO BID + Fluconazole PO BID | 50, 25 | 67 | 0.003 | NS** | |
| 11. Fluconazole PO BID | 25 | 53 | 0.003 | 0.002 | |

[1] Ultra Small Particle Size

*N = 5 mice per group; logrank (Mantel-Cox, univariate)

**NS = not statistically significant

TABLE 7

Number of CFU/g of Brain (Groups from Table 3)

| Group No. and Treatment | Mouse 1 | Mouse 2 | Mouse 3 | Mouse 4 | Mouse 5 |
|---|---|---|---|---|---|
| No Treatment | 15,400,000 | 7,300,000 | 17,800,000 | 9,800,000 | 6,000,000 |
| 1. FUNGIZONE ® IP + 5-FC Oral | 3,500,000 | 15,400,000 | 9,000,000 | 73,000,000 | 12,700,000 |
| 2. CAMB IP QD | 4,800,000 | 4,600,000 | 6,900,000 | 2,600,000 | 11,900,000 |
| 3. CAMB USPS[1] PO BID | 18,300,000 | 9,400,000 | 9,100,000 | 30,000,000 | 1,830,000 |
| 4. CAMB PO, QD | 14000 | 142,000 | 9,300,000 | 12,900,000 | 6,400,000 |
| 5. CAMB PO, BID | 14,000,000 | 21000 | 249,000 | 1,310,000 | 8,300,000 |
| 6. CAMB PO, QD + 5-FC oral | 5,200,000 | 9,200,000 | 8,600,000 | 3,900,000 | 3,400,000 |
| 7. CAMB PO BID + 5-FC oral | 20000 | 6,300,000 | 8,100,000 | 9,900,000 | 6,800,000 |
| 8. 5-FC oral | 10,800,000 | 8,500,000 | 7,300,000 | 15,000,000 | 5,800,000 |
| 9. CAMB PO QD + Fluconazole PO BID | 8,200,000 | 2,100,000 | 18,000,000 | 9,700,000 | 5,800,000 |
| 10. CAMB PO BID + Fluconazole PO BID | 16,200,000 | 11,700,000 | 7,500,000 | 5,700,000 | 31,000,000 |
| 11. Fluconazole PO BID | 4,200,000 | 4,300,000 | 3,900,000 | 6,800,000 | 11,300,000 |

[1]Ultra Small Particle Size

The invention claimed is:

1. A method of treating or preventing an infection due to a *Cryptococcus* spp., which method comprises: orally administering to a subject in need thereof
   (a) a cochleate composition comprising one or more cochleates and a therapeutically effective amount of a first antifungal compound, wherein the first antifungal compound is amphotericin B; and
   (b) a therapeutically effective amount of a second antifungal compound, wherein the second antifungal compound is selected from the group consisting of 5-Flucytosine, fluconazole, ketoconazole, ravuconazole, albaconazole, itraconazole, posaconazole, isavuconazole and voriconazole; wherein the first and second antifungal compounds are the only two antifungal compounds orally administered to the subject, and wherein the infection involves the central nervous system.

2. The method of claim 1, wherein the cochleate composition is administered daily for at least 7 days, at least 14 days, at least 21 days, or at least 28 days.

3. The method of claim 1, wherein the only two antifungal compounds are amphotericin B and 5-Flucytosine.

4. The method of claim 3, wherein the c5-Flucytosine is administered after the encochleated amphotericin B.

5. The method of claim 4, wherein the 5-Flucytosine is administered daily for at least 7 days, at least 14 days, at least 21 days, or at least 28 days.

6. The method of claim 1, wherein the infection is cryptococcal meningeoencephalitis.

7. The method of claim 1, wherein the infection is cryptococcal meningitis.

8. The method of claim 1, wherein the *Cryptococcus* spp. is *Cryptococcus neoformans*.

9. The method of claim 1, wherein the *Cryptococcus* spp. is *Cryptococcus gattii*.

10. The method of claim 1, wherein the subject is a human.

11. The method of claim 10, wherein the subject has HIV/AIDS, lymphoma, cirrhosis of the liver or has received an organ transplant.

12. The method of claim 1, wherein the antifungal compounds are delivered to the brain.

13. The method of claim 1, wherein preventing an infection due to a *Cryptococcus* spp., comprises preventing a recurrence of infection.

14. The method of claim 1, wherein preventing an infection due to a *Cryptococcus* spp., comprises treating a mammal or human, wherein the mammal or human is positive for a cryptococcal species antigen.

15. The method of claim 1, wherein the second antifungal compound is 5-Flucocytosine or fluconazole, wherein the 5-Flucocytosine or fluconazole is unencochleated.

16. The method of claim 10, wherein the second antifungal compound is 5-Flucocytosine, and wherein the 5-Flucocytosine is unencochleated.

17. The method of claim 10, wherein the second antifungal compound is fluconazole, and wherein the fluconazole is unencochleated.

* * * * *